United States Patent
Buisson et al.

(10) Patent No.: US 9,718,769 B2
(45) Date of Patent: Aug. 1, 2017

(54) PULVERULENT COMPOSITIONS OF A COMPLEX BETWEEN AN ACID AND A METAL AND METHOD OF PREPARATION THEREOF

(71) Applicant: INNOV'IA 3I, Pontaumur (FR)

(72) Inventors: Pierre Buisson, Lagord (FR); Robert Huet, Paris (FR); Sebastien Fournier, Andilly (FR); Jean-Eudes Vendeville, Perigny (FR)

(73) Assignee: INNOV'IA 3I, Pontaumur (FR)

( * ) Notice: Subject to any disclaimer, the term of this patent is extended or adjusted under 35 U.S.C. 154(b) by 6 days.

(21) Appl. No.: 14/385,229

(22) PCT Filed: Mar. 15, 2013

(86) PCT No.: PCT/FR2013/050549
§ 371 (c)(1),
(2) Date: Sep. 15, 2014

(87) PCT Pub. No.: WO2013/136030
PCT Pub. Date: Sep. 19, 2013

(65) Prior Publication Data
US 2015/0056452 A1    Feb. 26, 2015

(30) Foreign Application Priority Data
Mar. 16, 2012   (FR) .................................... 12 52423

(51) Int. Cl.
*C07C 51/41*   (2006.01)
*B32B 5/16*   (2006.01)
(Continued)

(52) U.S. Cl.
CPC .......... *C07C 323/58* (2013.01); *A23K 20/147* (2016.05); *A23K 20/22* (2016.05);
(Continued)

(58) Field of Classification Search
CPC ........................... C07C 51/412; C07C 51/418
(Continued)

(56) References Cited

U.S. PATENT DOCUMENTS

| 4,067,994 | A | 1/1978 | Anderson et al. |
| 4,142,059 | A | 2/1979 | Greene et al. |

(Continued)

FOREIGN PATENT DOCUMENTS

| DE | 19707380 A1 | 8/1998 |
| EP | 0100974 A1 | 2/1984 |

(Continued)

OTHER PUBLICATIONS

The Spheronization Process, spheronizer.com, 2008.*

(Continued)

*Primary Examiner* — Holly Le
(74) *Attorney, Agent, or Firm* — Young & Thompson

(57) ABSTRACT

Pulverulent compositions of a complex between an acid and a metal form an at least partially spherical particle. The acid is selected from 2-hydroxy-4-methyl-thiobutanoic acid (HMTBA), methionine, aspartic acid, the alginic acids, the pectinic acids, and the corresponding anions, in particular 2-hydroxy-4-methyl-thiobutanoate, methioninate, aspartate, the alginates and the pectinates. The metal is divalent or trivalent. The particle has an amorphous fraction the mass of which represents at least 50% of the total mass of the particle. The particle is substantially devoid of uncomplexed acid or anion and of uncomplexed metal or metal cation.

18 Claims, 5 Drawing Sheets

(51) Int. Cl.

| | |
|---|---|
| C07C 323/58 | (2006.01) |
| C07F 3/06 | (2006.01) |
| C07F 3/00 | (2006.01) |
| C07F 3/02 | (2006.01) |
| C07F 5/02 | (2006.01) |
| C07F 5/06 | (2006.01) |
| C07F 5/00 | (2006.01) |
| C07F 13/00 | (2006.01) |
| C07F 15/00 | (2006.01) |
| C07F 3/04 | (2006.01) |
| C07F 15/02 | (2006.01) |
| C07F 15/04 | (2006.01) |
| C07F 15/06 | (2006.01) |
| B01J 2/04 | (2006.01) |
| C07C 319/20 | (2006.01) |
| C07C 323/52 | (2006.01) |
| C07C 229/76 | (2006.01) |
| C08L 5/00 | (2006.01) |
| C07C 227/18 | (2006.01) |
| C07C 227/14 | (2006.01) |
| C07C 229/24 | (2006.01) |
| A23K 20/147 | (2016.01) |
| A23K 20/22 | (2016.01) |
| A23K 20/24 | (2016.01) |
| A23K 20/20 | (2016.01) |
| A23K 50/75 | (2016.01) |

(52) U.S. Cl.
CPC .............. *A23K 20/24* (2016.05); *A23K 20/30* (2016.05); *A23K 50/75* (2016.05); *B01J 2/04* (2013.01); *C07C 227/14* (2013.01); *C07C 227/18* (2013.01); *C07C 229/24* (2013.01); *C07C 229/76* (2013.01); *C07C 319/20* (2013.01); *C07C 323/52* (2013.01); *C07F 3/00* (2013.01); *C07F 3/006* (2013.01); *C07F 3/02* (2013.01); *C07F 3/04* (2013.01); *C07F 3/06* (2013.01); *C07F 5/00* (2013.01); *C07F 5/02* (2013.01); *C07F 5/06* (2013.01); *C07F 13/00* (2013.01); *C07F 15/0086* (2013.01); *C07F 15/02* (2013.01); *C07F 15/04* (2013.01); *C07F 15/06* (2013.01); *C08L 5/00* (2013.01); *Y10T 428/2982* (2015.01)

(58) Field of Classification Search
USPC ................................. 428/402; 562/400, 507
See application file for complete search history.

(56) References Cited

U.S. PATENT DOCUMENTS

| | | | |
|---|---|---|---|
| 4,335,257 A | 6/1982 | Cummins et al. | |
| 4,579,962 A | 4/1986 | Takano | |
| 6,287,627 B1* | 9/2001 | Binder | A23K 20/142 426/656 |
| 2006/0078597 A1 | 4/2006 | Jentzsch et al. | |
| 2006/0251765 A1 | 11/2006 | Lederman | |
| 2006/0287543 A1* | 12/2006 | Trehy | C07C 319/28 556/131 |
| 2011/0114745 A1 | 5/2011 | Buisson et al. | |
| 2013/0172617 A1* | 7/2013 | Le Thiesse | C07C 51/412 562/581 |

FOREIGN PATENT DOCUMENTS

| | | |
|---|---|---|
| EP | 0140865 A1 | 5/1985 |
| EP | 1176137 A1 | 1/2002 |
| EP | 1566373 A1 | 8/2005 |
| EP | 2161075 A1 | 3/2010 |
| FR | 1469803 A | 2/1967 |
| WO | 03011822 A2 | 2/2003 |
| WO | 2004012707 A1 | 2/2004 |
| WO | 2009125129 A2 | 10/2009 |

OTHER PUBLICATIONS

Lau et al., The evolution of pellet size and shape during spheronization of an extruded microcrystalline cellulose paste, Dec. 2013.*
Patel et al., "Spray Drying Technology: an Overview", Indian Journal of Science and Technology, 2009, vol. 2, No. 10, pp. 44-47.
International Search Report, dated Oct. 25, 2013, from corresponding PCT application.
French Search Report, dated Jan. 11, 2013, from corresponding FR application.

* cited by examiner

PULVERULENT COMPOSITIONS OF A COMPLEX BETWEEN AN ACID AND A METAL AND METHOD OF PREPARATION THEREOF

BACKGROUND OF THE INVENTION

Field of the Invention

The present invention relates to pulverulent compositions of a complex between an acid and a metal and the method of preparation thereof.

Description of the Related Art

Methionine, an essential amino acid, and HMTBA, an analogue of methionine, find very extensive applications in humans as a food supplement or medicinal product, as well as in animal feed. Their metal salts, for example the calcium, magnesium or zinc salts, in solid form, may be preferred. They can also make up for deficiencies of elements or trace elements. The best-known HMTBA salt is the dicalcium salt, comprising two moles of HMTBA equivalent per mole of calcium corresponding to the formula $(HMTBA)_2Ca$.

A method is known from EP140865A for preparing calcium salts of HMTBA, consisting of more than two and less than ten moles of HMTBA equivalent per mole of calcium. These salts are obtained by reacting HMTBA with a source of calcium selected from calcium oxide (CaO), calcium hydroxide $(Ca(OH)_2)$, calcium carbonate $(CaCO_3)$ as well as an HMTBA salt, for example the salt $(HMTBA)_2Ca$. HMTBA is generally in highly concentrated aqueous solution, with which the source of calcium is mixed, then the reaction medium thus obtained is dried at a temperature of the order of 70° C. The reaction medium of HMTBA with the source of calcium is, however, very viscous and sticky; it is therefore very difficult to homogenize in mixers or reactors equipped with conventional stirring systems, and at the end of reaction it is necessary to carry out drying in situ so as to be able to empty the reactor.

Recycling of HMTBA calcium salt, for example the salt $(HMTBA)_2Ca$, to the source of calcium before bringing it in contact with the HMTBA allows improvement in the consistency of the reaction medium and makes it easier to carry out the method as mentioned in EP140865A. But, as taught by U.S. Pat. No. 4,335,257, this improvement is observed for a proportion by weight of at least 20% of said salt relative to the reaction medium, and to achieve an acceptable consistency it may be necessary for this proportion to reach 80% of the reaction medium. Such a recycle ratio of finished product in the reaction medium reduces the productivity of an industrial installation considerably and necessitates appreciable oversizing of the mixer/reactor for a desired production capacity.

WO03/011822A2 proposes a method for preparing organic acid salts, in particular calcium salts, starting from said organic acid and calcium hydroxide and/or calcium oxide, in which the organic acid is deposited on an inert support before adding the source of calcium to it. Despite the presence of this support, it is essential to introduce the two reactants by successive addition in order to allow the reaction medium to dry between the two additions. This procedure greatly increases the residence time in the mixer and also requires considerable oversizing of said mixer for a given production capacity. Moreover, the inert support remains in the dry finished product, where it represents from 30 to 50 wt % of the total mass, which reduces the titre of active ingredient to that extent and thus generates extra costs in using the product (storage, transport, metering, etc.).

A solution that partly allows the aforementioned obstacles to be circumvented, but without requiring a support or other excipient, might be to use a simple method for preparing one or more HMTBA salts by means of an extruder. The advantage of such a method would be to perform rapid mixing of the acid and the metal in a short time and with shearing forces that would allow the HMTBA salt formed to be extruded without difficulty. However, a method of this type would lead to the formation of thin strands at the outlet from the extruder die that are incompatible with the particle sizes required in the end applications for the HMTBA salt, for example the production of animal feed products. Moreover, it would still be necessary to dry the product, which finally leads to adding two extra unit operations of drying and grinding of the HMTBA salt for it be usable.

FR 1469803, US 2006/0251765 and U.S. Pat. No. 6,287,627 describe methods for preparing salts between the anion of an acid and a metal cation, said method comprising a step for obtaining an aqueous solution of said salt, and a step of spray-drying of said aqueous solution.

These two-step methods make it possible to obtain salts in the form of powders, the granulometry of which allows direct use of said powders, for example for making animal feed products. However, the latter introduce, in addition to the reaction step, an additional step of drying. Moreover, they do not allow a high dry extract of the reaction medium; a high dry extract would lead to clogging of the equipment used.

SUMMARY OF THE INVENTION

Thus, a purpose of the present invention consists of providing complexes between an acid and a metal, without using a support or other excipient, in a single step.

Another purpose of the invention consists of providing, in a continuous process, complexes between an acid and a metal, in the form of stable powders that are easy to handle and are suitable for the application for which said complexes are intended.

Another purpose of the invention consists of providing a method allowing a high dry extract of the reaction medium, without clogging.

Another purpose of the invention consists of providing a method for preparing complexes between an acid and a metal, in a continuous process.

The invention consequently relates to a particle, essentially in the form of a homogeneous sphere or a fraction of a homogeneous sphere, essentially constituted by a complex, in particular a salt, between an acid or a corresponding anion and at least one metal or a corresponding metal cation, said particle being substantially devoid of uncomplexed acid or anion and of uncomplexed metal or metal cation, said acid being different from formic acid, acetic acid, and propionic acid, and said anion being different from formate, acetate and propionate.

By "particle" is meant a small monolithic element of matter that is all in one piece and which therefore does is not constituted by a juxtaposition of smaller elements.

By "homogeneous sphere" is meant a sphere or a spheroid in which said acid or anion, or said metal or cation, is not present in the pure state.

In particular, a homogeneous sphere is a sphere that only comprises a single complex between a particular acid and a particular metal, in particular only a single salt between a particular anion and a particular cation.

By "spheroid" is meant a solid the shape of which approaches that of a sphere.

By the expression "said acid or anion, or said metal or cation, in the pure state" is meant that said acid or anion, or said metal or cation, is not intimately mixed with said complex, but on the contrary forms at least one space where it is present in the pure state.

By "fraction of a homogeneous sphere" is meant any fragment originating from a broken homogeneous sphere.

By "metal according to the invention" is meant any element of the periodic table, capable of forming one or more cations, or a complex with an acid, and belonging to metal groups, in particular the alkali metals, alkaline-earth metals, transition metals and metalloids.

By "complex according to the invention" is meant a compound comprising at least one metal atom and at least one molecule of an acid as defined above, in which at least one atom of the molecule of acid is bound to the metal atom, or to the metal atoms for preparing mixed complexes, by a chemical bond or a chemical interaction. By way of illustration, one or more such bonds or one or more such chemical interactions are selected from ionic bonds, coordination bonds, van der Waals bonds etc. When the bond or the chemical interaction is an ionic bond, the complex is then a salt between an acid and a metal, respectively in the form of an anion corresponding to said acid at least once deprotonated and a metal cation, comprising an atom of said metal.

By "acid or corresponding anion" is meant the acid or an anion formed by at least one deprotonation of said acid.

By "metal or corresponding metal cation" is meant the metal or a cation comprising an atom of said metal.

The invention also relates to a particle, essentially in the form of a homogeneous sphere or a fraction of a homogeneous sphere, consisting essentially of a complex, in particular a salt, between an acid or a corresponding anion and at least one metal or a corresponding metal cation,
said acid or corresponding anion being selected from the group comprising 2-hydroxy-4-methyl-thiobutanoic acid (HMTBA), methionine, aspartic acid, the alginic acids, the pectinic acids, and the corresponding anions, in particular 2-hydroxy-4-methyl-thiobutanoate, methioninate, aspartate, the alginates and the pectinates,
said metal or metal cation being divalent or trivalent,
said particle having an amorphous fraction the mass of which represents at least 50%, in particular at least 70%, more particularly at least 90%, of the total mass of said particle,
said particle being substantially devoid of uncomplexed acid or anion and of uncomplexed metal or metal cation.

A complex according to the invention may be a compound comprising at least one metal atom and at least one molecule of an acid, in particular a compound comprising a metal atom and at least one molecule of an acid, in which:
an atom of the molecule of acid is bound to at least one metal atom, by a bond or chemical interaction, for example an ionic bond, and
another atom of the molecule of acid is bound to said metal atom, by the same type of bond or chemical interaction, for example an ionic bond.

A complex according to the invention may also be a compound comprising at least one metal atom and at least one molecule of an acid, in particular a compound comprising a metal atom and at least one molecule of an acid, in which:
an atom of the molecule of acid is bound to at least one metal atom, by a bond or chemical interaction, for example an ionic bond, and
another atom of the molecule of acid is bound to said metal atom, by another type of bond or chemical interaction, for example a coordination bond.

By way of illustration, a complex of the invention may be represented by the following formula (I):

$$(Acid)_n X_p Y_q \quad (I)$$

where X and Y represent, independently of one another, a metal,
n is an integer in the range from 1 to 10, and
p and q are integers in the range from 0 to 10, the sum of p and q being in the range from 1 to 10.

A complex between an acid or a corresponding anion and at least one metal or a corresponding metal cation according to the invention in particular denotes a salt, between an anion and a cation.

By way of illustration, a salt of the invention may be represented by the following formula (II):

$$(Acid^{k-})_n (X^{l+})_p (Y^{m+})_q \quad (II)$$

where:
X and Y represent, independently of one another, a metal,
k is an integer in the range from 1 to 7,
l and m are integers in the range from 1 to 7,
n is an integer in the range from 1 to 10, and
p and q are integers in the range from 0 to 10,
k, l, m, n, p and q being such that: $kn = lp + mq$.

Thus, "$Acid^{k-}$" represents an anion of an acid, said anion bearing k negative charges.
"$X^{l+}$" represents a metal cation bearing l positive charges.
"$Y^{m+}$" represents a metal cation bearing m positive charges.

In particular, a salt of the invention may be represented by the following formula (III):

$$(Acid^{k-})_n (X^{l+})_p \quad (III)$$

where:
X represents a metal,
k is an integer in the range from 1 to 7, k being in particular equal to 1,
l is an integer in the range from 1 to 7,
n is an integer in the range from 1 to 10, and
p is an integer in the range from 0 to 10, being in particular equal to 1,
k, l, n and p being such that: $kn = lp$.

Even more particularly, a salt of the invention may be represented by the following formula (IV):

$$(Acid^-)_l (X^{l+}) \quad (IV)$$

where:
X represents a metal,
l is an integer in the range from 1 to 7.

DETAILED DESCRIPTION OF THE INVENTION

According to an advantageous embodiment, the present invention relates to a particle consisting essentially of a complex, in particular a salt, said complex, in particular said salt, being able to be precipitated in an aqueous phase, said aqueous phase resulting from mixing a first aqueous medium, in particular an aqueous solution, containing said acid with a second aqueous medium, in particular a solution or an aqueous suspension containing said metal or cation, at a temperature ranging from ambient temperature to 100° C., the mass of said complex, in particular of the salt, to the total mass of said aqueous phase being in the range from 15 to 90%, in particular from 40 to 75%.

Thus, the first aqueous medium contains said acid. The second aqueous medium contains said metal or cation.

By "complex able to be precipitated in an aqueous phase" is meant that there is at least one temperature, in the range from ambient temperature to 100° C., and at least one mass ratio of complex to total mass of said aqueous phase, in the range 15 to 90%, in particular 40 to 75%, such that mixing of the first aqueous medium and of the second aqueous medium to form said aqueous phase causes precipitation of said complex in said aqueous phase.

By "precipitation of the complex in the aqueous phase" is meant the creation of a solid phase, comprising some or all of said complex, starting from said aqueous phase, and said aqueous phase may optionally still contain, after precipitation, a portion of the complex, in solution.

According to an advantageous embodiment, the present invention relates to a particle, essentially in the form of a homogeneous sphere or a fraction of a homogeneous sphere, in which said sphere is solid, hollow, or contains openings.

By "solid sphere" is meant a sphere formed of matter substantially devoid of cavities.

By "hollow sphere" is meant any sphere formed of matter provided with at least one cavity or vacuole.

By "sphere containing openings" is meant a hollow sphere of which at least one of the cavities or vacuole communicates with the exterior of said sphere.

Examples of such forms of particles may be found in Masters, K. *Spray drying Handbook*; Publ. Longman Scientific and Technical, 1988, p 323, FIGS. 8.5 a to f.

It should be noted that the particles illustrated in said work do not have the same composition as the particles of the present invention.

According to an advantageous embodiment, the present invention relates to a particle in which the ratio of the mass of said uncomplexed acid or anion and/or of said at least one uncomplexed metal or cation to the total mass of said particle is below 20%, and in particular is in the range from 0 to 5%, more particularly from 0 to 1%.

If the mass of said uncomplexed acid or anion is greater than 20%, the quantity of said uncomplexed acid or anion does not allow dry particles to be obtained and does not lead to a pulverulent composition being obtained. Moreover, the quantity of salt formed is no longer sufficient and does not allow the particles obtained to meet the requirements of the subsequent applications of said particles.

According to an advantageous embodiment, the ratio of the mass of said uncomplexed acid or anion to the total mass of said particle is zero (0%) and the mass of said metal or cation to the total mass of said particle is zero or between 0 and 5%, preferably between 0 and 1%, so as to ensure complete conversion of said acid.

According to an advantageous embodiment, the present invention relates to a particle in which, for any 1 µm² element considered on the surface of said particle, the ratio of the mass of said complex, in particular of said salt, to the total mass of the matter occupying said volume varies from 70% to 100%.

Said ratio may for example be measured by atomic analysis using scanning electron microscopy on an area of 1 µm².

If said ratio is below 70%, this reflects inhomogeneity of said particle, i.e. a non-homogeneous mixture between said acid or anion and said metal or cation at the scale of the particle.

Conversely, if said ratio is above 70%, the particle is regarded as homogeneous, i.e. the mixture between said acid or anion and said metal or cation is homogeneous at the scale of the particle.

According to an advantageous embodiment, the present invention relates to a particle having an amorphous fraction the mass of which represents at least 50%, in particular at least 70%, more particularly at least 90%, of the total mass of said particle.

"Amorphous" describes a compound in which the atoms do not display any medium and long distance ordering. Conversely, a crystalline compound is a compound in which the atoms are arranged in an ordered lattice and display medium and long distance ordering. Between these two extremes there are the semicrystalline compounds, also called partially amorphous compounds.

Thus, by "amorphous fraction" is meant the fraction of compound in amorphous form; an amorphous fraction of 0% corresponds to a crystalline compound whereas an amorphous fraction of 100% corresponds to an amorphous compound.

It is known that it is advantageous, in certain areas of industry, and in particular in the food-processing and pharmaceutical fields, to be able to have amorphous particles or particles with a high amorphous fraction. In fact, for particles the amorphous content of which is below 50%, subsequent phase transitions, in particular recrystallization of an amorphous phase during storage of a product comprising said particles, could greatly alter its dissolution kinetics as well as its bioavailability.

It is now well established that the amorphous or semicrystalline forms display better dissolution kinetics, and finally better bioavailability, than the crystalline forms of active ingredients that have very low solubility in aqueous media.

The amorphous fraction may be quantified by various techniques that are familiar to a person skilled in the art, described for example in Threlfall, T. L. *Analyst* 1995, 120, p. 2435-2459 or in Caira, M. R. *Topics in Current Chemistry* 1998, 198, p 163-208, such as X-ray diffraction or differential scanning calorimetry in isothermal mode.

According to an advantageous embodiment, the present invention relates to a particle in which said acid or corresponding anion is selected from the group comprising 2-hydroxy-4-methyl-thiobutanoic acid (HMTBA), methionine, aspartic acid, ascorbic acid, the alginic acids, the pectinic acids, and the corresponding anions, in particular 4-hydroxy-2-methyl-thiobutanoate, methioninate, aspartate, ascorbate, the alginates and the pectinates.

Said acid or corresponding anion is in particular selected from the group comprising 4-hydroxy-2-methyl-thiobutanoic acid (HMTBA), methionine, 2-hydroxy-4-methyl-thiobutanoate and methioninate.

According to an advantageous embodiment, the present invention relates to a particle in which said acid or corresponding anion is selected from the group comprising 2-hydroxy-4-methyl-thiobutanoic acid (HMTBA), methionine, aspartic acid, and the corresponding anions, in particular 2-hydroxy-4-methyl-thiobutanoate, methioninate, and aspartate, said metal or cation being in particular selected from Ca, Mg, and the corresponding cations, more particularly $Ca^{2+}$ and $Mg^{2+}$.

According to an advantageous embodiment, the present invention relates to a particle in which said complex is of the following formula (Ia):

$$(Acid)_n M \quad \text{(Ia)}$$

where M represents said metal, n being equal to 2 when said metal is divalent and equal to 3 when said metal is trivalent, said complex being in particular a salt, more particularly a salt of formula (HMTBA)$_2$Ca, (HMTBA)$_2$Mg, (HMTBA)$_2$Fe, (HMTBA)$_2$Mn, (HMTBA)$_2$Zn, (HMTBA)$_2$Cu, (HMTBA)$_3$Fe, (HMTBA)$_3$Al, (methionine)$_2$Ca, (methionine)$_2$Mg, (methionine)$_2$Fe, (methionine)$_2$Mn, (methionine)$_2$Zn, (methionine)$_2$Cu, (methionine)$_3$Fe, (methionine)$_3$Al, (aspartic acid)$_2$Ca, (aspartic acid)$_2$Mg, (aspartic acid)$_2$Fe, (aspartic acid)$_2$Mn, (aspartic acid)$_2$Zn, (aspartic acid)$_2$Cu, (aspartic acid)$_3$Fe, or (aspartic acid)$_3$Al, even more particularly a salt of formula (HMTBA)$_2$Ca, (HMTBA)$_2$Mg, (HMTBA)$_2$Fe, (HMTBA)$_2$Mn, (HMTBA)$_2$Zn, (HMTBA)$_2$Cu, (methionine)$_2$Ca, (methionine)$_2$Mg, (methionine)$_2$Fe, (methionine)$_2$Mn, (methionine)$_2$Zn, (methionine)$_2$Cu, (aspartic acid)$_2$Ca, (aspartic acid)$_2$Mg, (aspartic acid)$_2$Fe, (aspartic acid)$_2$Mn, (aspartic acid)$_2$Zn or (aspartic acid)$_2$Cu.

Thus, said acid and said metal may be supplied under stoichiometric conditions, i.e. in the proportions of formula (Ia), to form said complex of formula (Ia).

It should be noted, especially under industrial conditions, that the proportions of acid and of metal are likely to differ from these theoretical stoichiometric conditions: in any case, the possible difference is such that, in the particle considered, the ratio of the mass of said uncomplexed acid or anion and/or of said at least one uncomplexed metal or cation to the total mass of said particle is below 20%, and in particular is in the range from 0 to 5%, more particularly from 0 to 1%.

According to another advantageous embodiment, the present invention relates to a particle in which said complex is selected from the group consisting of the calcium alginates and calcium pectinates.

According to an advantageous embodiment, the present invention relates to a particle in which said complex is of the following formula (Ib):

(Acid)$_4$M          (Ib)

where M represents said metal,
said complex being in particular of formula (HMTBA)$_4$Ca.

Thus, to form said complex of formula (Ib), in particular (HMTBA)$_4$Ca, said acid and said metal may be supplied under hyperstoichiometric conditions, i.e. in the proportions of formula (Ib). These conditions are called hyperstoichiometric because the proportion of acid relative to the metal is higher in formula (Ib) than that encountered in the reference salt of formula (Ia), in particular (HMTBA)$_2$Ca.

According to an advantageous embodiment, the present invention relates to a particle in which said metal or corresponding cation is selected from the group comprising Li, Na, K, Mg, Be, Ca, Sr, Ba, Mn, Fe, Co, Ni, Cu, Zn, Pt, B, Al, Ga, In, and the corresponding cations, in particular Li$^-$, Na$^+$, K$^+$, Mg$^{2+}$, Be$^{2+}$, Ca$^{2+}$, Sr$^{2+}$, Ba$^{2-}$, Mn$^{2+}$, Fe$^{2+}$, Fe$^{3+}$, Co$^{2-}$, Co$^{3+}$, Ni$^{2+}$, Ni$^{3+}$, Cu$^{2+}$, Zn$^{2+}$, Pt$^{2+}$, Al$^{3+}$, Ga$^{3+}$ and In$^{3-}$.

According to an advantageous embodiment, the present invention relates to a particle in which said metal or corresponding cation is selected from the group comprising Mg, Be, Ca, Sr, Ba, Mn, Fe, Co, Ni, Cu, Zn, Pt, B, Al, Ga, In, in particular Mg, Ca, Fe, Mn, Cu, Zn and the corresponding cations, in particular Mg$^{2+}$, Be$^{2+}$, Ca$^{2+}$, Sr$^{2+}$, Ba$^{2+}$, Mn$^{2+}$, Fe$^{2+}$, Fe$^{3+}$, Co$^{2+}$, Co$^{3+}$, Ni$^{2+}$, Ni$^{3+}$, Cu$^{2+}$, Zn$^{2+}$, Pt$^{2+}$, Al$^{3+}$, Ga$^{3+}$, In$^{3+}$, more particularly Mg$^{2+}$, Ca$^{2+}$, Fe$^{2+}$, Fe$^{3+}$, Mn$^{2+}$, Cu$^{2+}$ and Zn$^{2-}$.

According to an advantageous embodiment, the present invention relates to a particle in which said metal or corresponding cation is selected from the group comprising Li, Mg, Ca, Fe, Mn, Cu and Zn and the corresponding cations, in particular Li$^+$, Mg$^{2+}$, Ca$^{2+}$, Fe$^{2+}$, Fe$^{3+}$, Mn$^{2+}$, Cu$^{2+}$ and Zn$^{2-}$.

According to an advantageous embodiment, the present invention relates to a particle in which said metal or corresponding cation is selected from the group comprising Mg, Ca, Cu and the corresponding cations, in particular Mg$^{2+}$, Ca$^{2+}$ and Cu$^{2+}$.

According to an advantageous embodiment, the present invention relates to a particle in which said metal is Li or the cation is Li$^+$.

According to an advantageous embodiment, the present invention relates to a particle in which said metal is Na or the cation is Na$^+$.

According to an advantageous embodiment, the present invention relates to a particle in which said metal is K or the cation is K$^+$.

According to an advantageous embodiment, the present invention relates to a particle consisting essentially of a salt between an anion of an acid and at least one metal cation.

According to an advantageous embodiment, the present invention relates to a particle in which said cation is selected from divalent and trivalent cations, and in particular is selected from Mg$^{2-}$, Be$^{2+}$, Ca$^{2+}$, Sr$^{2-}$, Ba$^{2+}$, Mn$^{2+}$, Fe$^{2+}$, Ca$^{2+}$, Ni$^{2+}$, Cu$^{2+}$, Zn$^{2-}$, Pt$^{2+}$, Fe$^{3-}$, Co$^{3+}$, Ni$^{3+}$, Al$^{3+}$, Ga$^{3+}$, and In$^{3+}$.

According to an advantageous embodiment, the present invention relates to a particle in which said cation is selected from Li$^|$, Mg$^{2|}$, Ca$^{2|}$, Fe$^{2|}$, Zn$^{2|}$, Mn$^{2|}$, Cu$^{2|}$ and Fe$^{3|}$.

According to an advantageous embodiment, the present invention relates to a particle in which said cation is Li$^+$.

According to an advantageous embodiment, the present invention relates to a particle in which said cation is Na$^+$.

According to an advantageous embodiment, the present invention relates to a particle in which said cation is K$^+$.

According to an advantageous embodiment, the present invention relates to a particle in which said anion is 2-hydroxy-4-methyl-thiobutanoate and said cation is Ca$^{2+}$.

According to an advantageous embodiment, the present invention relates to a particle in which said anion is methioninate or 2-hydroxy-4-methyl-thiobutanoate and said cation is selected from the group comprising Li$^+$, Mg$^{2+}$, Ca$^{2+}$, Fe$^{2+}$, Fe$^{3+}$, Zn$^{2+}$, Mn$^{2+}$ and Cu$^{2+}$, in particular Li$^+$, Mg$^{2+}$ and Ca$^{2+}$.

According to an advantageous embodiment, the present invention relates to a particle in which said anion is methioninate or 2-hydroxy-4-methyl-thiobutanoate and said cation is selected from the group comprising Mg$^{2+}$, Ca$^{2+}$, Fe$^{2+}$, Fe$^{3+}$, Zn$^{2+}$, Mn$^{2+}$ and Cu$^{2+}$, in particular Mg$^{2+}$ and Ca$^{2+}$.

According to an advantageous embodiment, the present invention relates to a particle in which said anion is methioninate or 2-hydroxy-4-methyl-thiobutanoate and said cation is Li$^+$.

According to an advantageous embodiment, the present invention relates to a particle in which said anion is methioninate or 2-hydroxy-4-methyl-thiobutanoate and said cation is Na$^+$.

According to an advantageous embodiment, the present invention relates to a particle in which said anion is methioninate or 2-hydroxy-4-methyl-thiobutanoate and said cation is K$^+$.

The invention also relates to a pulverulent composition of particles, said particles being as defined previously.

By "pulverulent composition of particles" is meant a solid, in a fractionated state, consisting of particles according to the present invention.

According to an advantageous embodiment, the granulometric size of said particles is in the range from 10 to 3000 µm, in particular from 20 to 300 µm, in granulometric average [Dv(0.5)].

By "granulometric average [Dv(0.5)]" is meant the average granulometric diameter, measured by laser diffraction, 50% of the particles of said composition having a diameter greater than said average diameter and 50% of the particles of said composition having a diameter less than said average diameter.

According to an advantageous embodiment, said pulverulent composition has a flowability index in the range from 4 to 18 [Flodex™ index].

The Flodex® method (Dow-Lepetit) measures the flowability (or ability to flow) of a powder. A sample is placed in a smooth cylinder having a circular hole in the bottom. The hole is sealed during filling. Once the total quantity of powder has been introduced, the bottom hole is opened. Powder having good flowability flows through a small hole, whereas powder having poor flowability requires a large hole to exit the cylinder. The Flodex™ flowability index is equal to the diameter, in millimeters, of the smallest hole through which the powder has fallen three times consecutively.

Moreover, said pulverulent composition has a density in the range from 150 g/L to 900 g/L, according to AFNOR standard NF V 04-344.

According to an advantageous embodiment, the present invention relates to a pulverulent composition in which, for a substantial portion of said composition, a particle of said portion is agglomerated with at least one other particle of said portion.

By "particle agglomerated with at least one other particle" is meant a particle that is juxtaposed or fused with at least one other particle, thus forming an agglomerate, i.e. a non-monolithic ensemble.

By the expression "for a substantial portion of said composition, a particle of said portion is agglomerated with at least one other particle of said portion" is meant that there is a portion of the composition in which a particle of said portion is agglomerated with at least one other particle of said portion, such that most of the finest particles of said composition are agglomerated with, adhere to or are fused with other particles of the composition, so that there is no longer more than 10% of fine particles of the composition smaller than 100 µm.

The invention also relates to the use of a pulverulent composition as described above, in animal feed.

The invention also relates to a method for preparing a pulverulent composition of particles consisting essentially of a complex, in particular a salt, between an acid or a corresponding anion and at least one metal or a corresponding metal cation, said method comprising a step of bringing said acid into contact with a mineral source of said metal or corresponding cation in a spray-drying tower in order to obtain the formation of said complex, in particular of said salt, and initiate its precipitation.

Surprisingly, the authors noticed that the kinetics of said precipitation was perfectly compatible with a spray-drying process despite a contact time not exceeding a few minutes, generally even less than a minute.

The authors were also surprised to find that a method according to the invention permitted a high dry extract of the reaction medium, without clogging, said reaction medium being obtained by said bringing into contact of said acid with a mineral source of said metal or corresponding cation.

The method according to the invention makes it possible to obtain said pulverulent composition after precipitation of said complex and drying of said pulverulent composition, and despite the exponential increase in viscosity observed during said precipitation.

Moreover, at the end of a process according to the invention, the pulverulent composition obtained can be handled directly, with good granulometry, where the possibility of recycling, in the context of forming of the pulverulent composition such as is carried out by a person skilled in the art in a multiple effect tower, does not in any way change the production capacities or the quality of the product resulting from the process, which makes it an extremely robust and productive process.

By "composition that can be handled directly" is meant a composition the flow of which allows handling, transfer, charging or discharging.

Finally, as spray-drying is extremely quick, no browning reaction occurs, such as is often observed with products already on the market, or already obtained by other methods.

Spray-drying according to the invention means a method of drying the reaction medium obtained by said bringing into contact of said acid with a mineral source of said metal or corresponding cation, by spraying said mixture in a stream of hot air using spraying devices such as nozzles, turbines or rotating disks. Drying and water transfer take place by entrainment in the air owing to the difference in vapour pressure between the droplet formed and the air at the periphery of the droplet.

It should be noted that spray-drying of a reaction medium as encountered in the present invention is called reactive spray-drying.

Various devices are suitable for reactive spray-drying according to the invention. As examples of devices for spray-drying, there may be mentioned toll form, single-effect drying towers, with internal or external fluidized air bed of the multiple effect tower type, well known to a person skilled in the art.

For example, in a single-effect tower with 10 kg/h evaporative capacity, a stoichiometric mixture of an acid, for example HMTBA, in an aqueous medium and a metallic source of a metal or cation, for example lime in suspension in water, in respective flow rates from 2 to 7 kg/h, with inlet temperatures from 180 to 100° C. and outlet temperatures from 150 to 65° C., it is possible to obtain 1 to 10 kg/h of pulverulent composition according to the invention.

Said device for reactive spray-drying according to the invention optionally comprises an additional spraying device for anti-agglomerating agent, for example via a powder metering device.

The invention also relates to a method for preparing a pulverulent composition of particles as described above, consisting essentially of a complex, in particular a salt, between an acid or a corresponding anion and at least one metal or a corresponding metal cation, said method comprising a step of bringing said acid into contact with a mineral source of said metal or corresponding cation in a spray-drying tower in order to obtain the formation of said complex, in particular of said salt, and initiate its precipitation, said acid or corresponding anion being selected from the group comprising 2-hydroxy-4-methyl-thiobutanoic acid (HMTBA), methionine, aspartic acid, the alginic acids, the pectinic acids, and the corresponding anions, in particular 2-hydroxy-4-methyl-thiobutanoate, methioninate, aspartate, the alginates and the pectinates,
said metal or metal cation being divalent or trivalent,
said particle having an amorphous fraction the weight of which represents at least 50%, in particular at least 70%, more particularly at least 90%, of the total weight of said particle.

According to an advantageous embodiment, a method according to the invention comprises a spraying step, during which precipitation of said complex, in particular of said salt, takes place.

According to a particularly advantageous embodiment, the contacting and spraying steps are carried out using the same device, in particular a device comprising a rotating spraying element, contacting being followed immediately by spraying.

By "contacting being followed immediately by spraying" is meant that, within one and the same device, a contacting means is linked directly to a spraying means.

The devices for carrying out, within them, the contacting step, followed immediately by the spraying step, are in particular, but non-limitatively, turbines or rotating disks such as described in patent application EP 2257380; contacting then takes place for example in a mixing chamber of a turbine, then, immediately after contacting, the complex thus formed is sprayed using said turbine.

According to another advantageous embodiment, a method according to the invention comprises a step of spray-drying of said complex, in particular of said salt, during which precipitation of said complex, in particular of said salt, proceeds until there is complete solidification of the particle.

According to another advantageous embodiment, a method according to the invention comprises the following steps:
bringing said acid into contact with a mineral source of said metal or corresponding cation in a spray-drying tower in order to obtain the formation of said complex, in particular of said salt, and initiate its precipitation;
spraying said complex, in particular said salt, undergoing precipitation, during which said precipitation continues, obtaining an ensemble of sprayed particles;
spray-drying said ensemble of sprayed particles, during which said precipitation continues until there is complete solidification of the particle, in order to obtain a stable pulverulent composition;
recovery of said pulverulent composition.

By "stable pulverulent composition" is meant a pulverulent composition that does not form lumps under normal storage conditions, such as a temperature below 20° C. and a relative humidity below 70%.

A stable pulverulent composition does not require subsequent grinding.

According to a particularly advantageous embodiment, a method according to the invention comprises the following steps:
bringing said acid into contact with a mineral source of said metal or corresponding cation in a spray-drying tower, using a device that allows said contacting, in order to obtain the formation of said complex, in particular of said salt, and initiate its precipitation;
spraying said complex, in particular said salt, undergoing precipitation, during which said precipitation takes place, using a spraying device, obtaining an ensemble of sprayed particles, said spraying immediately following the contacting, said spraying device being identical to that allowing the contacting, in particular a device comprising a rotating spraying element;
spray-drying said ensemble of sprayed particles, during which said precipitation continues until there is complete solidification of the particle, in order to obtain a stable pulverulent composition;
recovery of said pulverulent composition.

According to another advantageous embodiment, said contacting takes place by mixing an aqueous medium, in particular an aqueous solution, containing said acid and an aqueous medium, in particular a solution or an aqueous suspension containing said metal or cation.

A method according to the invention thus makes it possible to obtain said pulverulent composition when precipitation of the complex is initiated while bringing said acid into contact with a mineral source of said metal or corresponding cation, i.e. when the aqueous medium containing said acid and said metal or cation have high respective concentrations of acid and of metal, wherein precipitation of said complex is obtained. For the pulverulent composition to be obtained by separately carrying out the bringing in contact of said acid and said metal or cation, and then transforming the salt formed to powder form, it would be necessary to reach very low concentrations of acid and of metal, as is shown by the curve of precipitation time as a function of dry matter in the mixture, shown in FIG. 2, which would lead to conversion of the salt formed to powder form under very unfavourable economic conditions.

Thus, a method according to the invention makes it possible to work at high concentrations of acid, higher than in the methods in which precipitation of said mixture is undesirable and therefore is avoided in particular by using aqueous media containing said acid and/or aqueous media containing said metal or cation at relatively low concentrations.

The acid and said source of metal or cation, in particular said aqueous media containing respectively said acid and said metal or cation, are fed into said spraying devices in order to constitute said reaction mixture and produce said pulverulent composition there, after drying. It is of course within the general knowledge of a person skilled in the art to adapt the characteristics of said devices.

The choice of spraying device will in particular be designed to provide, concomitantly or otherwise, mixing of said aqueous media, and said spraying.

The optimum conditions of time, temperature, and energy required for said spraying depend on the chemical nature of the reactants, i.e. said acid and said source of metal or cation, and the chemical nature of said complex that is required, and will be determined from case to case by a person skilled in the art.

The feed rates of said two reactants, acid and source of metal or cation, are regulated as a function of their respective chemical nature and the type of complex required.

The spraying devices are preferably, but non-limitatively, high-pressure spraying nozzles, single-fluid or two-fluid, with external or internal mixing, in which the carrier fluid may be air, a neutral gas or steam or a mixture of these fluids; turbines, inverted-cups or rotating disks as described in patent application EP 2257380 may be used.

The spraying devices, made up of the spraying feed line and the spraying element, will preferably be designed to ensure a minimum residence time necessary for the formation of the complex and initiation of precipitation of said complex.

In order to increase the effectiveness of contacting, it may be advantageous to add a mixing chamber before or during spraying to ensure a relatively short contact time before spraying, of a few minutes at most.

According to an advantageous embodiment, said contacting takes from 400 ms to 5 minutes, in particular from 5 to 30 seconds.

According to an advantageous embodiment, said contacting takes from 100 ms to 5 minutes, in particular from 100 ms to 30 s.

According to another advantageous embodiment, the temperature during said contacting and until said spraying varies from ambient temperature to 150° C., preferably between 40 and 120° C., even more preferably between 60 and 95° C.

According to another advantageous embodiment, the pressure during said contacting and until said spraying varies from atmospheric pressure to 600 bar.

The mixing chamber may be equipped with a suitable internal mixing device.

According to an advantageous embodiment, said contacting is carried out in a device such as static or dynamic mixers, in particular kneaders, extruders, and mixers without an internal component, such as ultrasonic mixers.

The whole of the spray-drying device, in particular the spraying devices described above, makes it possible to optimize production of the pulverulent composition with very high degrees of conversion of the reactants.

The final pulverulent composition, in the form of a dry powder with controlled granulometry, is thus recovered directly in a single pass, without the need for any additional handling.

In order to obtain a pulverulent composition with even more uniform granulometry, the drying device may be supplemented with the injection of the fine particles originating from the method directly in the spraying zone or by using spray devices of the rotating disk type as described in patent application EP 2257380 for more efficient control of the aerosol generated.

The use of a drying tower in which the residence time is as long as possible, from a few seconds to several minutes, is preferred. The method is advantageously carried out in a tower of the multiple effect type or very high toll form type, with a fluidized air bed incorporated at the bottom of the equipment and external fluidized bed air dryer depending on the application of the end product, the expected water content and by incorporating the kinetics of precipitation of the complex obtained.

According to another advantageous embodiment, a method according to the invention comprises an additional step of agglomeration.

Thus, agglomeration may be carried out by spraying water with a spraying nozzle, on a bed of pulverulent composition for example of 500 g on a fluidized air bed of the Glatt GPCG1 type, with a fluidization air flow rate of 150 to 300 m³/h, a flow rate of spray water from 2 to 20 g/min with an inlet temperature from 40 to 120° C. and an outlet temperature from 25 to 100° C.

According to another advantageous embodiment, said spray-drying tower is a multiple effect spray-drying tower, said drying step also comprising agglomeration.

Thus, drying and agglomeration may advantageously be carried out on a tower of the MSD type with 100 to 400 kg/h of evaporative capacity, by spraying said aqueous media in the drying tower comprising a static bed at the bottom of the tower according to FIG. 1 with spraying flow rates from 50 to 500 kg/h, inlet temperatures from 100 to 250° C. and outlet temperatures from 40 to 150° C.

According to another advantageous embodiment, said bringing of said acid into contact with a mineral source of said metal or corresponding cation is carried out continuously.

According to another advantageous embodiment, said acid or corresponding anion is selected from the group comprising 2-hydroxy-4-methyl-thiobutanoic acid (HMTBA), methionine, aspartic acid, ascorbic acid, the alginic acids, the pectinic acids, and the corresponding anions, in particular 2-hydroxy-4-methyl-thiobutanoate, methioninate, aspartate, ascorbate, the alginates and the pectinates.

According to an advantageous embodiment, the invention relates to a method as described above, in which said acid or corresponding anion is selected from the group comprising 2-hydroxy-4-methyl-thiobutanoic acid (HMTBA), methionine, aspartic acid, and the corresponding anions, in particular 2-hydroxy-4-methyl-thiobutanoate, methioninate, and aspartate, said metal or cation being in particular selected from Ca, Mg, and the corresponding cations, more particularly $Ca^{2+}$ and $Mg^{2+}$.

According to an advantageous embodiment, the invention relates to a method as described above, in which said complex is of the following formula (Ia):

$$(\text{Acid})_n M \quad (\text{Ia})$$

where M represents said metal, n being equal to 2 when said metal is divalent and to 3 when said metal is trivalent, said complex being in particular a salt, more particularly a salt of formula $(HMTBA)_2Ca$, $(HMTBA)_2Mg$, $(HMTBA)_2Fe$, $(HMTBA)_2Mn$, $(HMTBA)_2Zn$, $(HMTBA)_2Cu$, $(HMTBA)_3Fe$, $(HMTBA)_3Al$, $(methionine)_2Ca$, $(methionine)_2Mg$, $(methionine)_2Fe$, $(methionine)_2Mn$, $(methionine)_2Zn$, $(methionine)_2Cu$, $(methionine)_3Fe$, $(methionine)_3Al$, $(aspartic\ acid)_2Ca$, $(aspartic\ acid)_2Mg$, $(aspartic\ acid)_2Fe$, $(aspartic\ acid)_2Mn$, $(aspartic\ acid)_2Zn$, $(aspartic\ acid)_2Cu$, $(aspartic\ acid)_3Fe$, or $(aspartic\ acid)_3Al$, even more particularly a salt of formula $(HMTBA)_2Ca$, $(HMTBA)_2Mg$, $(HMTBA)_2Fe$, $(HMTBA)_2Mn$, $(HMTBA)_2Zn$, $(HMTBA)_2Cu$, $(methionine)_2Ca$, $(methionine)_2Mg$, $(methionine)_2Fe$, $(methionine)_2Mn$, $(methionine)_2Zn$, $(methionine)_2Cu$, $(aspartic\ acid)_2Ca$, $(aspartic\ acid)_2Mg$, $(aspartic\ acid)_2Fe$, $(aspartic\ acid)_2Mn$, $(aspartic\ acid)_2Zn$ or $(aspartic\ acid)_2Cu$.

According to another advantageous embodiment, the present invention relates to a method in which said complex is selected from the group consisting of the calcium alginates and calcium pectinates.

According to an advantageous embodiment, the invention relates to a method as described above, in which said complex is of the following formula (Ib):

$$(\text{Acid})_4 M \quad (\text{Ib})$$

where M represents said metal, said complex being in particular of formula $(HMTBA)_4Ca$.

According to another advantageous embodiment, said metal or corresponding cation is selected from the group comprising Li, Na, K, Mg, Be, Ca, Sr, Ba, Mn, Fe, Co, Ni, Cu, Zn, Pt, B, Al, Ga, In and the corresponding cations, in particular $Li^+$, $Na^+$, $K^+$, $Mg^{2+}$, $Be^{2+}$, $Ca^{2+}$, $Sr^{2+}$, $Ba^{2+}$, $Mn^{3+}$, $Fe^{2+}$, $Fe^{3+}$, $Co^{2+}$, $Co^{3+}$, $Ni^{2+}$, $Ni^{3+}$, $Cu^{2+}$, $Zn^{2+}$, $Pt^{2+}$, $Al^{3+}$, $Ga^{3+}$ and $In^{3+}$.

According to a particularly advantageous embodiment, said metal or corresponding cation is selected from the group comprising Li, Mg, Ca, Fe, Mn, Cu and Zn and the corresponding cations, in particular $Li^+$, $Mg^{2+}$, $Ca^{2+}$, $Fe^{2-}$, $Fe^{3+}$, $Mn^{2+}$, $Cu^{2+}$ and $Zn^{2+}$.

According to an advantageous embodiment, the invention relates to a method as described above, in which said metal or corresponding cation is selected from the group comprising Mg, Be, Ca, Sr, Ba, Mn, Fe, Co, Ni, Cu, Zn, Pt, B, Al, Ga, In, in particular Mg, Ca, Fe, Mn, Cu, Zn and the corresponding cations, in particular $Mg^{2+}$, $Be^{2+}$, $Ca^{2+}$, $Sr^{2-}$, $Ba^{2+}$, $Mn^{2+}$, $Fe^{2+}$, $Fe^{3+}$, $Co^{2+}$, $Co^{3+}$, $Ni^{2+}$, $Ni^{3+}$, $Cu^{2+}$, $Zn^{2+}$, $Pt^{2+}$, $Al^{3+}$, $Ga^{3+}$, $In^{3+}$, more particularly $Mg^{2+}$, $Ca^{2+}$, $Fe^{2+}$, $Fe^{3+}$, $Mn^{2+}$, $Cu^{2+}$ and $Zn^{2+}$.

According to an advantageous embodiment, the invention relates to a method as described above, in which said metal or corresponding cation is selected from the group comprising Mg, Ca, Cu and the corresponding cations, in particular $Mg^{2+}$, $Ca^{2+}$ and $Cu^{2+}$.

According to an advantageous embodiment, the invention relates to a method in which said metal is Li or the cation is $Li^+$.

According to an advantageous embodiment, the invention relates to a method in which said metal is Na or the cation is $Na^+$.

According to an advantageous embodiment, the invention relates to a method in which said metal is K or the cation is $K^+$.

According to a particularly advantageous embodiment, said particles consist essentially of a salt between an anion of an acid and at least one metal cation.

According to another advantageous embodiment, said cation is selected from divalent and trivalent cations, and in particular is selected from $Mg^{2+}$, $Be^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Pt^{2+}$, $Fe^{3+}$, $Co^{3+}$, $Ni^{3+}$, $Al^{3+}$, $Ga^{3+}$, and $In^{3+}$.

According to a particularly advantageous embodiment, said cation is selected from $Li^+$, $Mg^{2+}$, $Ca^{2-}$, $Fe^{2+}$, $Zn^{2+}$, $Mn^{2+}$, $Cu^{2+}$ and $Fe^{3+}$.

According to an advantageous embodiment, the invention relates to a method in which said cation is $Li^+$. According to an advantageous embodiment, the invention relates to a method in which said cation is $Na^+$.

According to an advantageous embodiment, the invention relates to a method in which said cation is $K^+$.

According to an advantageous embodiment, the invention relates to a method in which said anion is methioninate or 2-hydroxy-4-methyl-thiobutanoate and said cation is selected from the group comprising $Mg^{2+}$, $Ca^{2+}$, $Fe^{2+}$, $Fe^{3+}$, $Zn^{2+}$, $Mn^{2+}$ and $Cu^{2+}$, in particular $Mg^{2+}$ and $Ca^{2+}$.

According to an advantageous embodiment, the invention relates to a method in which said anion is methioninate or 2-hydroxy-4-methyl-thiobutanoate and said cation is $Li^+$.

According to an advantageous embodiment, the invention relates to a method in which said anion is methioninate or 2-hydroxy-4-methyl-thiobutanoate and said cation is $Na^+$.

According to an advantageous embodiment, the invention relates to a method in which said anion is methioninate or 2-hydroxy-4-methyl-thiobutanoate and said cation is $K^+$.

According to another advantageous embodiment, said mineral source of said metal or cation is selected from the metal hydroxides, the milks of metal hydroxide, the metal oxides and the corresponding metal carbonates.

According to another advantageous embodiment, said mineral source of said metal or cation is of natural origin.

According to another particularly advantageous embodiment, said anion is 2-hydroxy-4-methyl-thiobutanoate and said cation is $Ca^{2+}$, the source of $Ca^{2+}$ being selected from lime, milk of lime, slaked lime, calcium hydrogen carbonate and calcium carbonate.

According to another advantageous embodiment, said source of $Ca^{2+}$ is $Ca(OH)_2$.

According to another advantageous embodiment, said anion is methioninate or 2-hydroxy-4-methyl-thiobutanoate and said cation is selected from the group comprising $Li^+$, $Mg^{2+}$, $Ca^{2+}$, $Fe^{2+}$, $Fe^{3+}$, $Zn^{2+}$, $Mn^{2+}$ and $Cu^{2+}$, the source of said cation being selected from oxide, hydroxide, an aqueous solution of hydroxide and the carbonate of said cation.

The invention also relates to a particle obtainable by the method described above.

The invention also relates to an ensemble of particles obtainable by the method described above.

The invention also relates to the agglomerates obtainable by the method described above.

Figure 1:
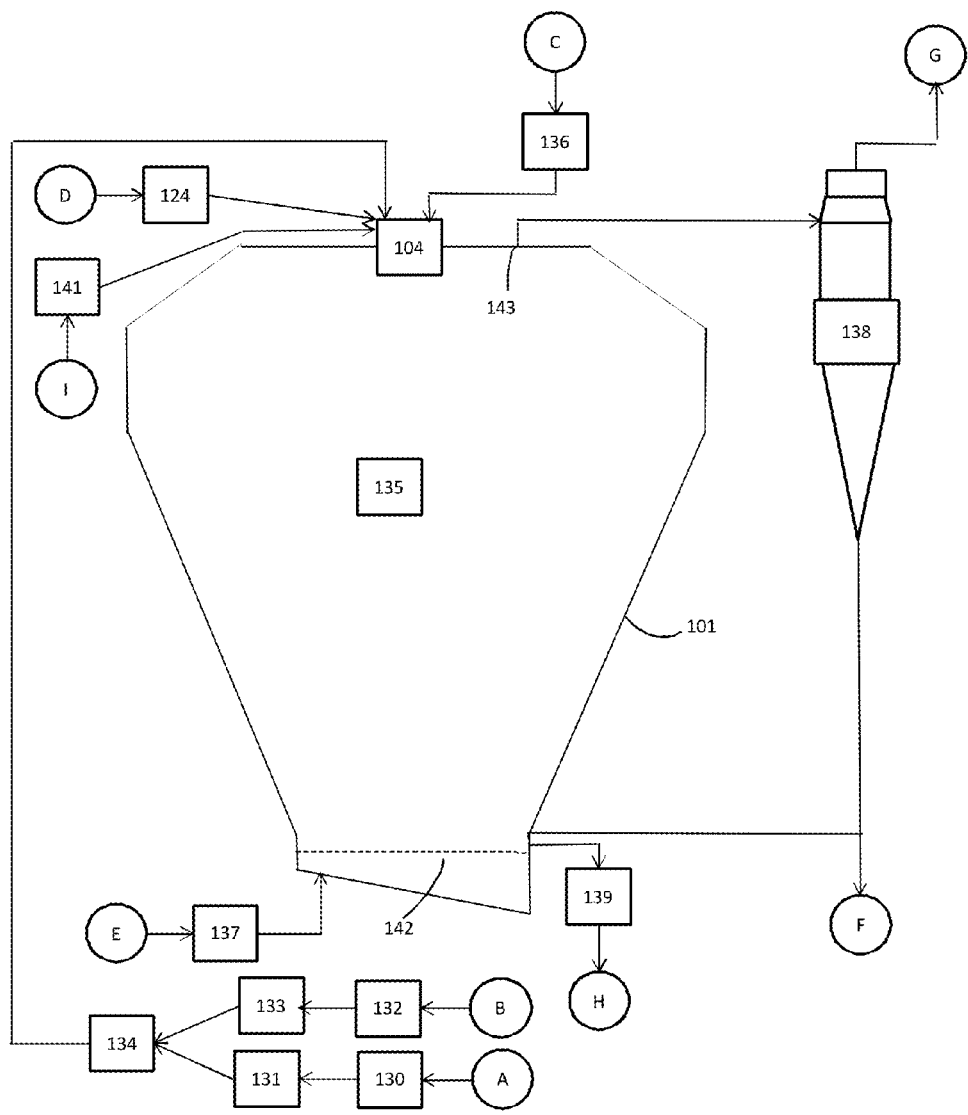
FIG. 1 is a schematic diagram of a method according to the invention, carried out in a multiple effect tower.

An aqueous medium containing an acid, represented by circle A, optionally passes through a heater 130 and feeds, by a pump 131, the contacting device 134. An aqueous medium containing a metal or metal cation represented by circle B optionally passes through a heater 132 and feeds, by a pump 133, the contacting device 134. The aqueous phase resulting from mixing aqueous medium A with aqueous medium B is sprayed in the spray tower via spraying device 104 intended for the production of monodisperse or polydisperse aerosols.

Circle C represents an additional spraying device for anti-agglomerating agent via a powder metering device 136, if necessary.

Circle D represents introduction of the hot carrier gas in the spray-drying version, via fan 124.

Circle E represents introduction of the secondary carrier gas, for drying and/or final cooling of the stabilized final composition obtained, solid or undergoing solidification, via a fan 137.

A cyclone 138 separates some or all of the end product F, i.e. the pulverulent composition, which is recovered, and the carrier gas G, which is discharged.

An external vibrated fluidized bed 139 may also be provided for recovering some or all of the end product H, i.e. the pulverulent composition, from the bottom of the tower.

Secondary air E is introduced through a permeable bottom 142 of tower 135 to bring the pulverulent material into the form of a fluidized bed. The used air is discharged via an orifice 143 provided, through the top wall of vessel 101. In this example, the used air then passes through cyclone 138, which produces on the one hand particles of product F and on the other hand air to be discharged G. Most of the particles are collected just above the permeable wall 142. FIG. 1 shows that the particles are collected either directly at F, or via the external fluidized bed 139 at H when one is provided.

Moreover, it is also possible to provide the addition, represented by circle I, in the spraying zone, of a substance in powder form, in particular fine particles of the pulverulent composition recovered at the outlet of cyclone 138, product F, or from the installation, injected by means of device 141 mainly consisting of a powder metering device.

Figure 2:
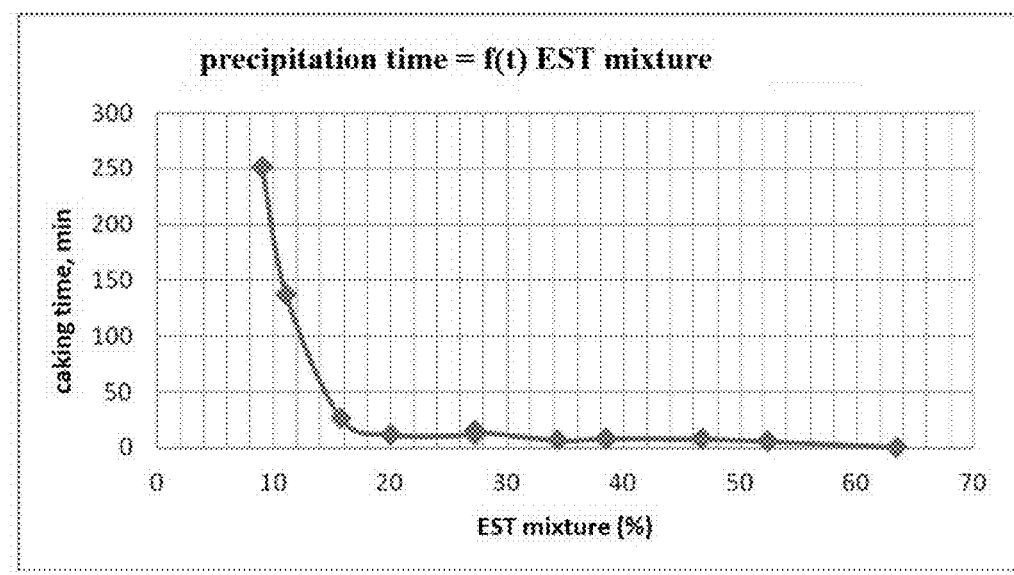

FIG. 2 is a graph showing the precipitation time (in minutes) of a mixture of milk of lime and HMTBA, as a function of the total dry extract of said mixture (as a percentage).

Figure 3:
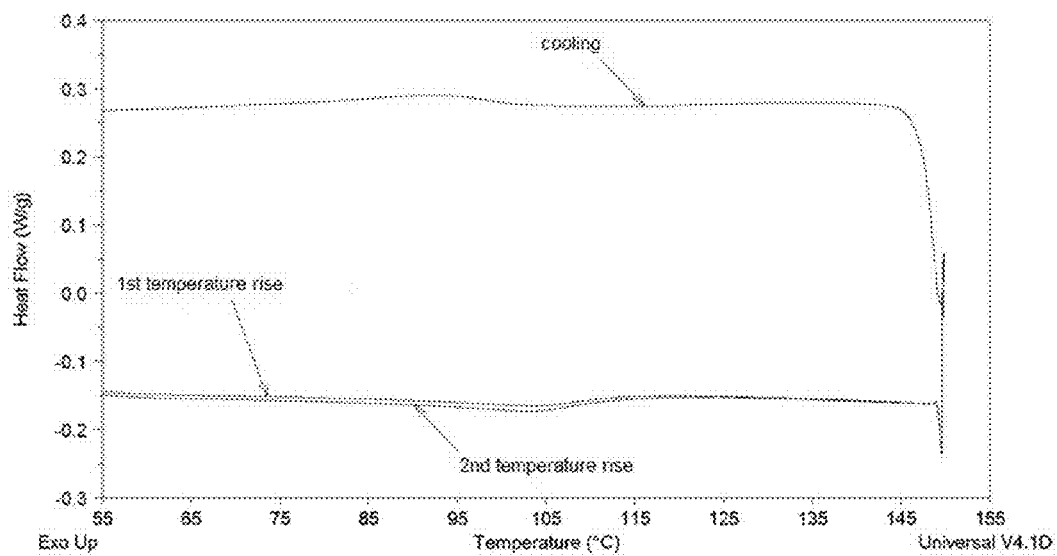

FIG. 3 is a graph relating to sample "R", showing the heat flow as a function of temperature, measured by differential scanning calorimetry (DSC) in isothermal mode.

A melting peak is noted at 103° C. when the temperature rises, and a crystallization peak at 92° C. (start of the peak at 102° C.) when the temperature falls.

Figure 4:
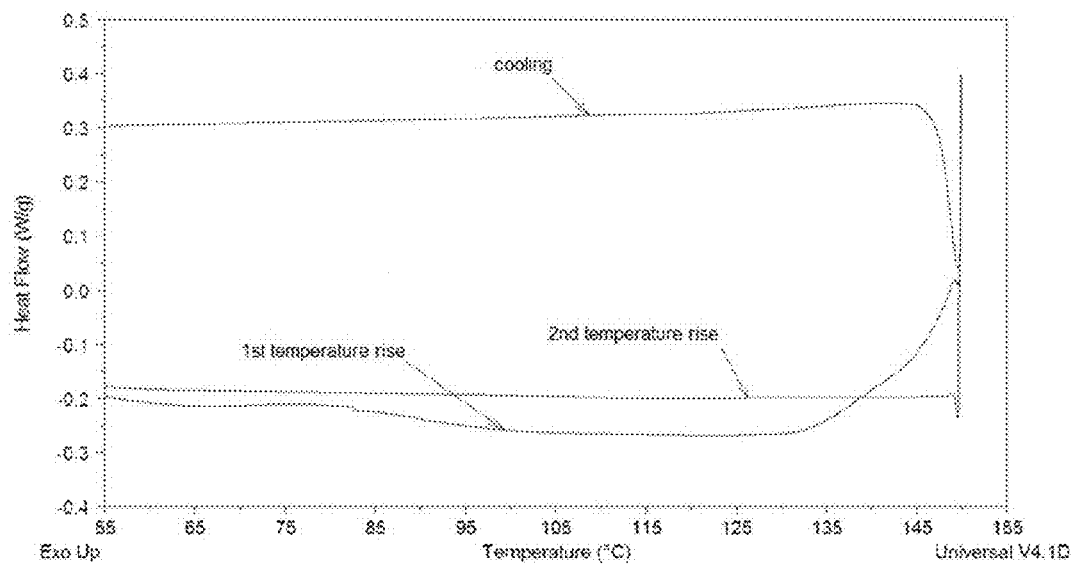

FIG. 4 is a graph relating to sample "T7", representing heat flow as a function of temperature, measured by differential scanning calorimetry (DSC) in isothermal mode.

An endothermic peak of very small amplitude is noted at 82° C. when the temperature rises, followed by an extended endothermic region that is not characteristic of fusion peaks. No thermal effect is observed when the temperature falls, therefore there is absence of recrystallization of the product.

Figure 5A:
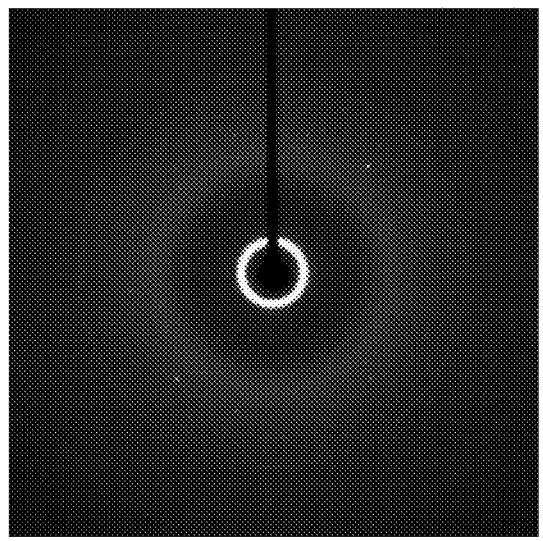

FIG. 5a shows the 2D diffraction pattern obtained for sample "T7".

Figure 5B:
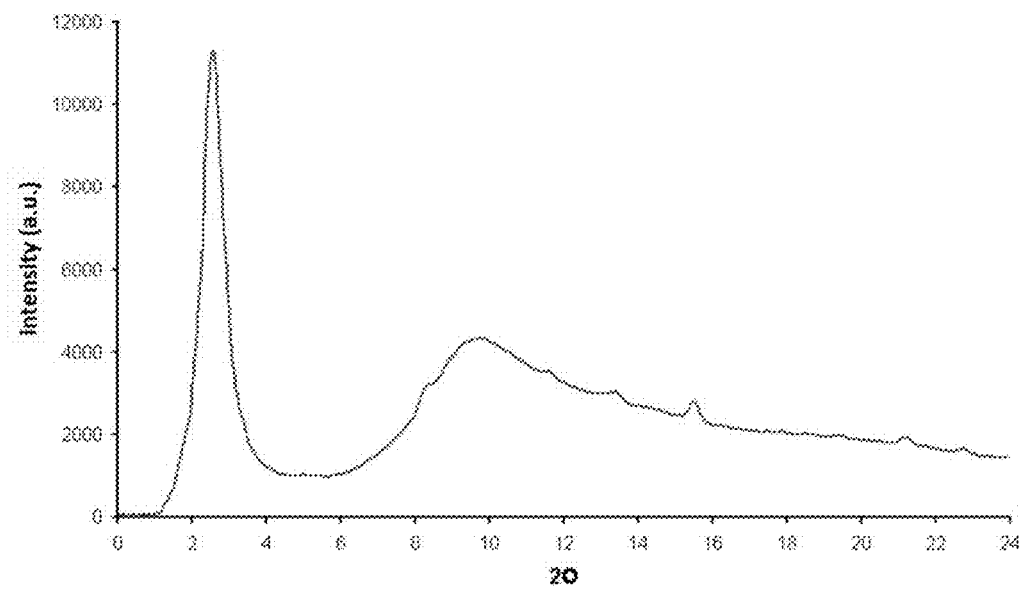

FIG. 5b shows the powder pattern obtained for sample "T7".

Figure 6A:
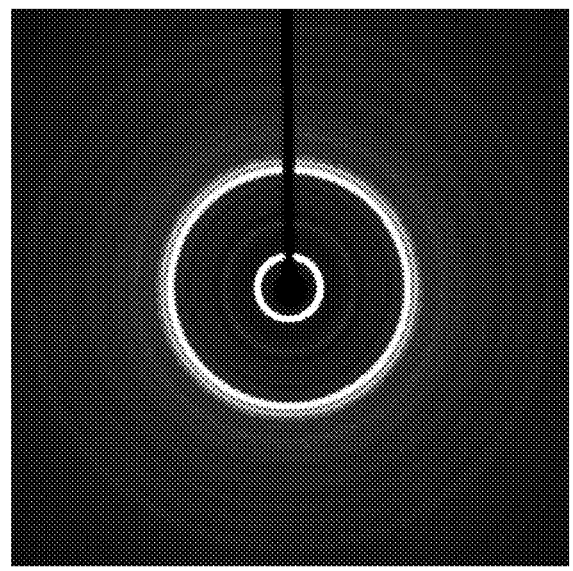

FIG. 6a shows the 2D diffraction pattern obtained for sample "R".

Figure 6B:
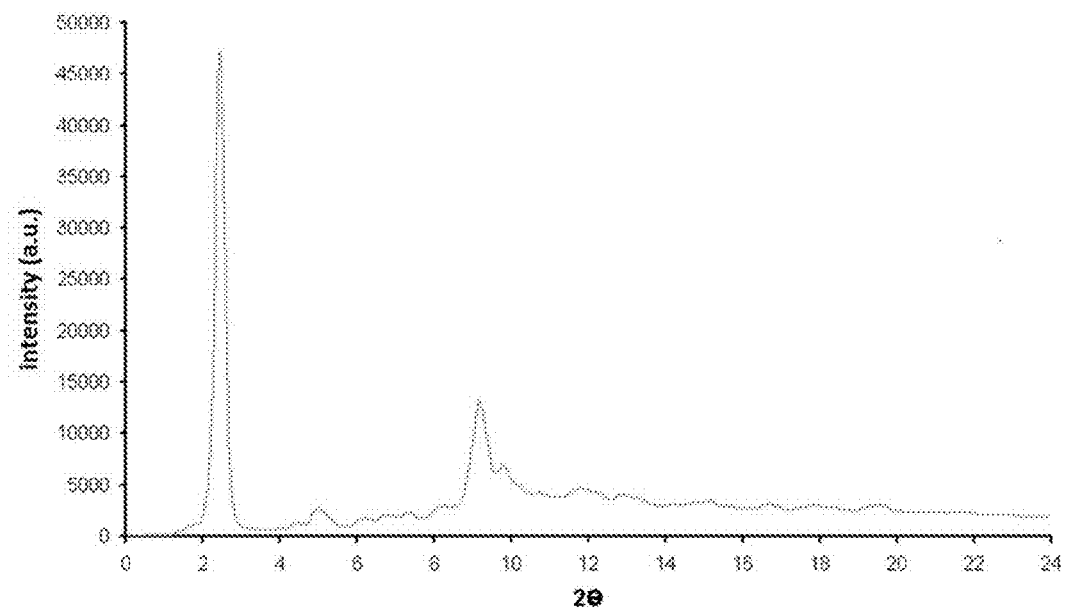

FIG. 6b shows the powder pattern obtained for sample "R".

Samples T7 and R were analysed by X-ray diffraction using a Bruker APEX-II Quasar diffractometer equipped with a molybdenum microsource ($\lambda=0.71073$ Å).

Each sample was ground beforehand in a mortar for two minutes.

Each of the powders thus obtained is then transferred to a capillary with diameter of 0.5 mm that is transparent to X-rays, and is then mounted on a goniometer.

The recording characteristics are perfectly identical for each sample, namely:
  distance from the detector: 80 mm
  recording time: 999 s
  uniform rotation of the sample about the Phi axis of 359° during acquisition
  position of the angles Chi, Kappa and Omega=0°
  recording temperature 280 K The 2D diffraction patterns obtained for each of the samples correspond to FIGS. 5a and 6a.

Angular grouping of these two-dimensional images was then performed using XRD2DScan 4.1.1 software, after subtracting from each image that of the background noise recorded under the same conditions, to obtain the curves shown in FIGS. 5b and 6b.

The invention is illustrated by examples 1 to 9 given below.

EXAMPLES

Example 1: Preparation of the Salt (HMTBA)$_2$Ca

Milk of lime prepared at 30% dry matter is mixed continuously in a pipeline containing a static mixer with a solution of HMTBA at 88% dry matter in the ratio 22.2% of lime (calculation based on the dry matter used) and 77.8% of HMTBA (calculation based on the dry matter used).

The contacting time is 7 seconds.

The reaction medium is then sprayed using a nozzle according to the knowledge of a person skilled in the art, in a single effect spray tower with an inlet temperature of 140° C. and an outlet temperature of 79° C.

The product is then processed in a fluidized air bed dryer to obtain an agglomerated powder to simulate a multiple effect spray tower.

The product obtained has a content of HMTBA of 81.4%, of $Ca^{2+}$ 11.8%, and a water content of 1.3%. The average granulometry is 240 μm and the density is 300 g/L.

Example 2: Another Preparation of the Salt (HMTBA)$_2$Ca

Milk of lime prepared at 30% dry matter is mixed continuously in a pipeline containing a static mixer at 138 kg/h with a solution of HMTBA at 88% dry matter at 154 kg/h to give a reaction medium of 60% dry matter.

The contacting time is 15 seconds.

The reaction medium is sprayed using a nozzle according to the knowledge of a person skilled in the art, in a single effect spray tower with an inlet temperature of 185° C. and an outlet temperature of 128° C.

The product obtained contains 84.9% of HMTBA, 12.0% of $Ca^{2+}$ and 0.5% of water.

The average granulometry is 156 μm (Dv(0.5) in laser granulometry), and the density is 170 g/l.

Example 3: Preparation of a Mg Salt of HMTBA

A suspension of magnesium hydroxide at 20% dry matter is mixed continuously in a pipeline containing a static mixer at 2.9 kg/h, with a solution of HMTBA at 70% dry matter at 4.3 kg/h.

The contacting time during reactive spraying is 7 seconds.

The reaction medium is then sprayed using a nozzle according to the knowledge of a person skilled in the art in a single effect spray tower with an inlet temperature of 140° C. and an outlet temperature of 76° C.

The product obtained has a content of HMTBA of 91.2%, a content of $Mg^{2+}$ of 7.4% and a water content of 1.4%.

The average granulometry is 7 μm and the density is 310 g/L.

Example 4: Preparation of a Li Salt of HMTBA

Milk of lithium hydroxide prepared at 10% dry matter is mixed continuously in a pipeline containing a static mixer at 3.6 kg/h with a solution of HMTBA at 70% dry matter at 4.0 kg/h.

The contacting time is 7 seconds.

The reaction medium is then sprayed using a nozzle according to the knowledge of a person skilled in the art in a spray tower with an inlet temperature of 160° C. and an outlet temperature of 70° C.

The product obtained contains 89.2% of HMTBA, 4.2% of $Li^+$ and 6.6% of water.

The average granulometry is 5 μm, and the density is 360 g/L.

Example 5: Preparation of the Salt (HMTBA)$_2$Ca Using an Atomizing Turbine

Milk of lime prepared at 20% dry matter is mixed continuously in an atomizing turbine (of the NIRO Atomizer type) at 3.9 kg/h with a solution of HMTBA at 70% dry matter at 3.4 kg/h.

The contacting time is 120 milliseconds.

The product is then atomized in a single effect spray tower with an inlet temperature of 140° C. and an outlet temperature of 90° C.

The product obtained has a content of HMTBA of 85.0%, of $Ca^{2+}$ 10.7%, and a water content of 1.3%.

The average granulometry is 43 μm and the density is 380 g/L.

Example 6: Preparation of a Methionine Salt

Milk of lime prepared at 20% dry matter is mixed continuously in a pipeline containing a static mixer with a solution of methionine at 20% dry matter.

The contacting time is 7 seconds. The flow rate of the milk of lime is 1.5 kg/h and that of the methionine solution is 6.0 kg/h.

The reaction medium is then sprayed using a nozzle according to the knowledge of a person skilled in the art in a single effect spray tower with an inlet temperature of 160° C. and an outlet temperature of 75° C.

The product obtained has a content of HMTBA of 86.9%, of $Ca^{2+}$ 11.7%, and a water content of 1.3%.

The average granulometry is 35 μm and the density is 300 g/L.

Example 7: Preparation of a Salt $(HMTBA)_2Ca$ by a Method Not According to the Present Invention, and Comparison of the Product Obtained with a Product According to the Invention An HMTBA salt is prepared by addition, in a vessel, of 100 g of HMTBA at 88% dry matter, and 88 g of milk of lime containing 25% dry matter.

Mixing is carried out by stirring with a propeller mixer for 20 seconds.

The mixture obtained is left to crystallize for 20 h at ambient temperature and then dried in a stove at 105° C. for 24 h.

The product "R" thus obtained is ground in a mortar.

The conditions for production of sample "R" make it possible to obtain a crystallized HMTBA salt.

This product "R" as well as an HMTBA salt obtained under the conditions for carrying out example 2 called "T7" are analysed by X-ray diffraction and by differential scanning calorimetry (DSC) in isothermal mode.

FIG. 3 obtained by DSC shows that sample R has a low-energy endothermic peak when the temperature rises as well as an exothermic peak when the temperature falls. These two peaks reflect respectively the melting of crystals and then the recrystallization of these crystals during cooling.

A second temperature cycle gives the same endo- and exothermic effects, confirming that it is indeed a reversible phenomenon of melting and crystallization. No other thermal effects are seen during these temperature cycles.

It is deduced from this that compound "R" is a 100% crystalline compound.

For the compound of the invention analysed by DSC, FIG. 4 shows that an endothermic peak of very small amplitude is observed at 82.39° C., which might correspond to a glass transition phenomenon (typical of amorphous systems) followed by extended endothermic effects not characteristic of fusion peaks. No thermal effect is observed when the temperature falls, therefore there is no recrystallization of the product after the 1st temperature rise.

It may be concluded that in contrast to sample "R", the sample of the invention is in mainly amorphous form.

These same samples were analysed by X-ray diffraction.

FIGS. 5b and 6b show that the first peak is much wider for sample T7 than for sample "R". This indicates that there is short-range order but not long-range order as suggested by the absence of subsequent peaks (in particular those at 5° and 9.2°). This indicates a completely amorphous sample, with only short-range order. The degree of crystallinity would then be close to 0%.

Example 8: Another Preparation of the Salt $(HMTBA)_2Ca$

Milk of lime prepared at 26.2% dry matter is mixed continuously by means of an ultrasonic mixing device at 126 kg/h with a solution of HMTBA at 88% dry matter at 143 kg/h to give a reaction medium with 59% dry matter.

The contacting time is 20 seconds.

The reaction medium is sprayed using a nozzle according to the knowledge of a person skilled in the art, in a single effect spray tower with an inlet temperature of 200° C. and an outlet temperature of 136° C.

The product obtained contains 83.5% of HMTBA, 12.3% of $Ca^{2+}$ and 2.7% of water.

Example 9: Another Preparation of the Salt $(HMTBA)_2Ca$

Milk of lime prepared at 45% dry matter is mixed continuously in a pipeline containing a static mixer with a solution of HMTBA at 88% dry matter in the ratio 20% of lime (calculation based on the dry matter used) and 80% of HMTBA (calculation based on the dry matter used).

The contacting time is 7 seconds.

The reaction medium is then sprayed using a nozzle according to the knowledge of a person skilled in the art, in a single effect spray tower with an inlet temperature of 160° C. and an outlet temperature of 90° C.

The product obtained has a content of HMTBA of 85.3%, of $Ca^{2+}$ 11.1%, and a water content of 1.7%. The average granulometry is 40 μm and the density is 380 g/L.

Example 10: Preparation of a Sodium Salt of Aspartic Acid

A solution of sodium hydroxide at 50% concentration by weight is mixed continuously in a pipeline containing a static mixer at 1.4 kg/h with a suspension of aspartic acid at 20% concentration by weight at 11.6 kg/h.

The contacting time is 15 seconds. The product is then atomized in a single effect spray tower with an inlet temperature of 180° C. and an outlet temperature of 95° C.

The product obtained is a stable, flowable white powder, with good solubility in water. The average granulometry is 55 μm, the water content is 2.3% and the solution pH is 6.5.

Example 11: Preparation of a Calcium Salt of Aspartic Acid

Milk of lime prepared at 30% dry matter is mixed continuously in a pipeline containing a static mixer at 1.9 kg/h with a suspension of aspartic acid at 20% concentration by weight at 10.4 kg/h.

The contacting time is 15 seconds. The product is then atomized in a single effect spray tower with an inlet temperature of 180° C. and an outlet temperature of 90° C.

The product obtained is a stable, flowable white powder, with good solubility in water. The average granulometry is 35 μm, the water content is 2.9% and the solution pH is 6.8.

Example 12: Preparation of a Salt of (HMTBA) of Type 4

Milk of lime prepared at 30% dry matter is mixed continuously in a pipeline containing a static mixer at 70 kg/h with a solution of HMTBA at 88% dry matter at 193 kg/h.

The contacting time is 15 seconds. The product is then atomized in a multiple effect spray tower with an inlet temperature of 180° C., an outlet temperature of 95° C., and recycling of fine particles to the spraying zone.

The product obtained has a content of 91.6% HMTBA, 5.7% calcium, and a water content of 1.5%.

Example 13: Preparation of a Cu Salt of HMTBA

A suspension of copper hydroxide at 35% dry matter is mixed continuously in a pipeline containing a static mixer at 2.8 kg/h, with a solution of HMTBA at 88% dry matter at 3.5 kg/h.

The contacting time during reactive spraying is 8 seconds.

The reaction medium is then sprayed using a nozzle according to the knowledge of a person skilled in the art in a single effect spray tower with an inlet temperature of 140° C. and an outlet temperature of 80° C.

The product obtained has a content of HMTBA of 81.8%, a content of $Cu^{2+}$ of 15.4% and a water content of 1.2%.

The average granulometry is 40 μm and the density is 420 g/L.

Example 14: Use of a $(HMTBA)_2Ca$ Salt According to the Invention for Feeding Laying Hens Summary Laying hens were fed either with DL-methionine (DLM), or with an HMTBA-Ca salt according to the invention, or with a combination (50/50) of the two for 6 weeks. The laying performance and the parameters relating to the eggs were measured throughout the 6 weeks.

HMTBA-Ca is as effective as DLM for most of the parameters, but improves laying efficiency (consumption index or average weight of the eggs). HMTBA-Ca helps to obtain a higher weight of albumin than that obtained with DLM.

The combination of HMTBA-Ca and DLM gives intermediate results for the performance parameters or the parameters relating to the eggs.

Experimental Conditions

Eighty laying hens aged 45 weeks were housed for 6 weeks and were distributed at random into three equal groups (20 per group). Each hen was kept in an individual cage at a temperature of (20±2° C.) with controlled lighting conditions. All the hens were offered a similar basic diet, with or without addition of DLM, of HMTBA-Ca or of a 50/50 mixture (HMTBA-Ca: DLM) (Tables 1 and 2) to give a supplement in methionine equivalent of 0.13% for all the food compositions. All the laying hens had free access to drinking water and were fed throughout the 6-week period of the experiment. The egg laying performance, including the components of the eggs, was measured throughout the 6-week period.

TABLE 1

Composition of the feed (%)

| Raw material | Group 1 % | Group 2 % | Group 3 % |
|---|---|---|---|
| Maize | 50 | 50 | 50 |
| Wheat | 16.1 | 16.1 | 16.1 |
| Soya cake 48 | 22.07 | 22.07 | 22.07 |
| Soya oil | 0.95 | 0.95 | 0.95 |
| DL-Methionine (NP99) | 0.13 | 0 | 0.07 |
| HMTBA-Ca | 0 | 0.15 | 0.08 |
| Limestone | 8.12 | 8.12 | 8.12 |
| Calcium hydrogen phosphate | 1.48 | 1.48 | 1.48 |
| Salt | 0.35 | 0.35 | 0.35 |
| Premix | 0.8 | 0.8 | 0.8 |
| Total | 100 | 100 | 100 |

Nutrients

| | Group 1 | Group 2 | Group 3 |
|---|---|---|---|
| Crude proteins (%) | 16.5 | 16.5 | 16.5 |
| Metabolizable energy (kcal/kg) | 2730 | 2730 | 2730 |
| Calcium (%) | 3.508 | 3.508 | 3.508 |
| Available phosphorus (%) | 0.331 | 0.331 | 0.331 |
| Dig. Methionine (%) | 0.37 | 0.37 | 0.37 |
| Dig. M + C (%) | 0.603 | 0.603 | 0.603 |
| Dig. Lysine (%) | 0.722 | 0.722 | 0.722 |

TABLE 2

Levels of methionine supplementation: expected and measured (%)

| | Group 1 | Group 2 | Group 3 |
|---|---|---|---|
| Total methionine (%) | 0.35 | 0.24 | 0.28 |
| Methionine added (%) | 0.11 | 0.00 | 0.06 |
| HMTBA added (%) | 0.00 | 0.11 | 0.07 |
| Total in methionine equivalent (%) | 0.35 | 0.35 | 0.35 |

Laying Performance and Results Relating to the Characteristics of the Eggs

Data relating to laying performance and the composition of the eggs (albumen and yolk) are presented in Table 3 below.

The laying hens fed with the HMTBA-Ca salt produce a higher daily weight of eggs than those fed with DLM, as the average weight of the eggs with HMTBA-Ca is 2.3% higher relative to that obtained with DLM. The proportion of albumen and yolk is not significantly affected by the source of methionine, but the eggs of the hens fed with HMTBA-Ca contain more albumen (+3%) relative to the eggs of the hens fed with DLM.

TABLE 3

Results relating to the different methionine supplements.

|  | Group 1 DLM | | Group 2 HMTBA-Ca | | Group 3 50/50 mixture | | ANOVA |
|---|---|---|---|---|---|---|---|
|  | Mean | Standard error | Mean | Standard error | Mean | Standard error | p value |
| Initial body weight (g/hen) | 1724.7 | 126.7 | 1738.6 | 135.6 | 1729.3 | 110.5 | 0.94 |
| Daily food intake (g/day) | 112.4 | 8.1 | 112.7 | 5.9 | 113.0 | 5.9 | 0.97 |
| Laying frequency (%) | 95% | 5% | 95% | 4% | 96% | 4% | 0.63 |
| Average weight of the eggs (g/egg) | 63.4 | 4.0 | 64.9 | 3.6 | 64.1 | 3.1 | 0.47 |
| Weight of eggs (g/day) | 60.3 | 4.2 | 62.0 | 4.6 | 61.8 | 4.0 | 0.41 |
| Albumen (g/egg) | 38.38 | 2.78 | 39.53 | 2.67 | 39.14 | 2.69 | 0.71 |
| Yolk (g/egg) | 16.38 | 1.08 | 16.47 | 0.95 | 16.18 | 1.07 | 0.74 |
| Consumption index (g feed/g egg) | 1.87 | 0.12 | 1.82 | 0.12 | 1.83 | 0.10 | 0.44 |
| Final body weight (g/hen) | 1834.9 | 98.0 | 1897.2 | 150.0 | 1850.2 | 112.8 | 0.28 |

Example 15: Use of a (HMTBA)$_2$Ca Salt According to the Invention for Feeding Growing Chickens Summary Growing chickens were supplemented (0.3%) either with DLM, or with HMTBA or with HMTBA-Ca salt according to the invention, for 46 days. HMTBA and more particularly HMTBA-Ca showed the best growth performance. Moreover, HMTBA-Ca showed far better digestibility of the nutrients than that obtained with the other two forms of methionine.

Experimental Conditions

One hundred and forty-seven commercial chickens (1 day old, 48 g) were housed from day 1 to day 46, including the starting phase (days 1-21) and the finishing phase (days 22-46). All the chickens were randomly distributed in seven equal groups (21 per group), and each group was made up of three subgroups of 7 birds each. Each subgroup was kept in an enclosure at a temperature of (28±2° C.), with controlled lighting conditions. All the chickens were offered a similar basic diet, with or without addition of DLM, HMTBA or HMTBA-Ca at levels of 0 (control) or 0.3% in the starting phase and 0 or 0.24% in the finishing phase (Table 4). All the chickens had free access to food and drinking water throughout the test period of 46 days. The weight of the chickens was measured every week and food intake was monitored throughout the experiment.

The excrement of the chickens was collected for the 3 days following the 42$^{nd}$ day of the experiment, were frozen and stored (at −20° C.) for later chemical analyses.

At the end of the experiment, the birds were weighed individually and sacrificed. The abdominal fat, the muscles of the thigh and of the breast were taken, lyophilized and weighed.

TABLE 4

Composition of the feed

| Composition (%) | Starting phase (days 0-21) | Finishing phase (days 21-46) |
|---|---|---|
| Maize | 50.42 | 49.72 |
| Soya cake | 37.00 | 32.00 |
| Wheat | 4.00 | 8.00 |
| NaCl | 0.34 | 0.34 |
| Calcium hydrogen phosphate | 1.90 | 1.50 |
| Limestone | 1.00 | 1.10 |
| Choline | 0.04 | 0.04 |
| Oil | 5.00 | 7.00 |
| Sources of methionine[1] | 0-0.30 | 0-0.24 |
| Premix, vitamins-minerals[2] | 0.30 | 0.30 |
| Composition of nutrients | | |
| ME, Mcal/kg | 3.04 | 3.18 |
| CP, % | 20.97 | 19.27 |
| Lys, % | 1.12 | 1.10 |
| Met + cysteine, % | 0.67 | 0.63 |
| Met | 0.33 | 0.31 |
| P available, % | 0.44 | 0.37 |
| Ca, % | 0.97 | 19.27 |
| P total, % | 0.69 | 0.61 |

[1]HMTBA, DLM or HMTBA-Ca
[2]per kg of feed: vitamin A (retinol acetate), 1500 IU; cholecalciferol, 200 IU; vitamin E (DL-α-tocopherol), 10 IU; riboflavin, 3.5 mg, pantothenic acid, 10 mg; niacin, 30 mg; cobalamin, 10 g, choline chloride, 1000 mg; biotin, 0.15 mg, folic acid, 0.5 mg, thiamine, 1.5 mg; pyridoxine, 3.0 mg, Fe, 80 mg; Zn, 40 mg, Mn, 60 mg, I, 0.18 mg; Cu, 8 mg; Se, 0.15 mg.

Results

Performance Relating to Growth and Composition of the Carcasses

Data relating to the growth performance and composition of the carcasses are summarized in Tables 5 and 6. The final body weight and the gain in body weight are significantly higher in the chickens fed with HMTBA 0.3% relative to the control group. There is no significant difference in food supply for the seven groups, but a lower consumption index was observed in the HMTBA 0.3% group. In the course of the experiment, the weight of the muscles of the thigh and breast of the chickens fed with HMTBA or HMTBA-Ca was significantly higher than those fed with DLM. No significant difference was observed for the weight of the abdominal fat as a function of the source of methionine, apart from an increase in the percentage of abdominal fat in the group supplemented with HMTBA-Ca (0.3%).

TABLE 5

Results relating to supplementation with DLM,
HMTBA or HMTBA-Ca for 46-day-old chickens*.

| Group | Final body weight (kg/chicken) | Gain in body weight (g/chicken/day) | Food intake (g/chicken/day) | Feeding:gain (g:g) |
| --- | --- | --- | --- | --- |
| Control | $3.05 \pm 0.10^a$ | $67.85 \pm 2.26^a$ | $134.85 \pm 3.72$ | $1.99 \pm 0.01$ |
| 0.3% DLM | $3.17 \pm 0.15^{ab}$ | $70.47 \pm 3.37^{ab}$ | $141.51 \pm 0.24$ | $2.01 \pm 0.10$ |
| 0.3% HMTBA | $3.44 \pm 0.02^b$ | $76.41 \pm 0.40^b$ | $142.23 \pm 8.46$ | $1.86 \pm 0.12$ |
| 0.3% HMTBA-Ca | $3.38 \pm 0.28^{ab}$ | $75.08 \pm 6.18^{ab}$ | $144.53 \pm 20.93$ | $1.91 \pm 0.12$ |

*The values are expressed as mean ± standard deviation. Each group represents 21 chickens at age 46 days.
$^{a,b,c}$Within one and the same column, the values with different superscripts are significantly different (P < 0.05).

TABLE 6

Effect of DLM, HMTBA or HMTBA-Ca on the composition of the carcass of the 46-day chickens*.

| Group | DL (g) | PDL (%) | DB (g) | PDB (%) | PDAT (%) |
| --- | --- | --- | --- | --- | --- |
| Control | $549.42 \pm 15.32^a$ | $20.31 \pm 0.16^{ab}$ | $521.69 \pm 64.00^a$ | $20.88 \pm 1.63^{ab}$ | $1.77 \pm 0.62^a$ |
| 0.3% DLM | $586.03 \pm 23.43^{ab}$ | $20.12 \pm 0.22^a$ | $596.88 \pm 56.68^{abc}$ | $22.77 \pm 1.44^b$ | $1.88 \pm 0.43^a$ |
| 0.3% HMTBA | $648.98 \pm 27.92^c$ | $21.98 \pm 0.97^c$ | $669.66 \pm 50.16^c$ | $22.77 \pm 1.44^b$ | $2.07 \pm 0.63^{ab}$ |
| 0.3% HMTBA-Ca | $588.64 \pm 38.07^{ab}$ | $22.06 \pm 1.64^c$ | $617.54 \pm 45.21^{bc}$ | $22.98 \pm 3.00^b$ | $2.49 \pm 0.59^b$ |

DL, weight of the muscles of the thigh
DB, weight of the muscles of the breast
PDL, ratio of the weight of the muscles of the thigh (without bone or skin) to that of the eviscerated chicken
PDB, ratio of the weight of the muscles of the breast (without bone or skin) to that of the eviscerated chicken
PDAT, ratio of the weight of the abdominal fat to that of the eviscerated chicken
*The values are expressed as mean ± standard deviation. Each group represents 21 chickens at age 46 days.
$^{a,b,c}$Within one and the same column, the values with different superscripts are significantly different (P < 0.05).

Apparent Digestibility

As shown in Table 7, the diets supplemented with methionine equivalent led to a significant increase in apparent digestibility of the dry matter, of the crude proteins and crude fats in the chickens, in the order HMTBA-Ca>HMTBA>DLM. However, the apparent digestibility of ash was significantly lower than for the control groups. The diets containing HMTBA-Ca or HMTBA gave improvements in apparent digestibility relative to diets containing DLM, this being mainly due to the overall higher activity of the digestive enzymes in the duodenum and the jejunum.

TABLE 7

Apparent digestibility (%) of dry matter, crude proteins, crude fats and ash, in 46-day chickens supplemented with DLM, HMTBA or HMTBA-Ca*.

| Group | dry matter | crude proteins | crude fats | Ash |
| --- | --- | --- | --- | --- |
| Control | $68.39 \pm 1.31^a$ | $44.23 \pm 2.95^a$ | $81.93 \pm 1.90^a$ | $86.03 \pm 3.98^d$ |
| 0.3% DLM | $78.22 \pm 1.70^c$ | $63.70 \pm 2.85^{cd}$ | $86.15 \pm 0.93$ | $56.02 \pm 1.01^b$ |
| 0.3% HMTBA | $79.02 \pm 1.61^{cd}$ | $62.40 \pm 2.89^{cd}$ | $87.80 \pm 1.39^{bc}$ | $55.83 \pm 0.16^b$ |
| 0.3% HMTBA-Ca | $81.80 \pm 0.32^d$ | $66.44 \pm 0.37^{cd}$ | $90.28 \pm 0.20^c$ | $44.62 \pm 0.89^a$ |

*The values are expressed as mean ± standard deviation for 10 chickens.
$^{a,b,c}$Within one and the same column, the values with different superscripts are significantly different (P < 0.05).

CONCLUSION

The present study shows that diets comprising HMTBA-Ca or HMTBA lead to improvement in growth and in the composition of the carcass relative to diets containing DLM. The diet supplemented with HMTBA-Ca (0.3%) led to the highest weight of muscles of the thigh and breast, relative to the other groups. Moreover, the diet supplemented with HMTBA-Ca led to a greater apparent digestibility relative to the group supplemented with DLM. The results show that supplementation with HMTBA or HMTBA-Ca led to an increase in the gain in body weight, and in the weight of the muscles of the thigh and breast in the absence of any reduction in food intake by induction of the activity of the digestive enzymes and by regulation of intestinal absorption of essential nutrients.

The invention claimed is:
1. A spray-dried particle, comprising:
   a spray-dried homogeneous sphere or a fraction of a spray-dried homogeneous sphere, being formed of a complex or a salt, between an acid or a corresponding anion and at least one metal or a corresponding metal cation,
   said acid or corresponding anion being selected from the group consisting of 2-hydroxy-4-methyl-thiobutanoic acid (HMTBA), methionine, aspartic acid, alginic acids, pectinic acids, corresponding anions, 2-hydroxy-4-methyl-thiobutanoate, methioninate, aspartate, alginates and pectinates,
   said metal or metal cation being divalent or trivalent,
   said spray-dried particle having an amorphous fraction a mass of which represents at least 50% of a total mass of said spray-dried particle, said spray-dried particle being substantially devoid of uncomplexed acid or anion and of uncomplexed metal or metal cation.

2. The spray-dried particle according to claim 1, wherein a ratio of at least one of a mass of uncomplexed acid or anion or of said at least one uncomplexed metal or cation to the total mass of said spray-dried particle is below 20%.

3. The spray-dried particle according to claim 2, wherein said complex has the following formula (Ia):

$$(\text{Acid})_n M \qquad\qquad (\text{Ia})$$

where M represents said metal,
n being equal to 2 when said metal is divalent and to 3 when said metal is trivalent,
said complex being a salt of formula (HMTBA)$_2$Ca, (HMTBA)$_2$Mg, (HMTBA)$_2$Fe, (HMTBA)$_2$Mn, (HMTBA)$_2$Zn, (HMTBA)$_2$Cu, (HMTBA)$_3$Fe, (HMTBA)$_3$Al, (methionine)$_2$Ca, (methionine)$_2$Mg, (methionine)$_2$Cu, (methionine)$_3$Fe, (methionine)$_3$Al, (aspartic acid)$_2$Ca, (aspartic acid)$_2$Mg, (aspartic acid)$_2$Fe, (aspartic acid)$_2$Mn, (aspartic acid)$_2$Zn, (aspartic acid)$_2$Cu, (aspartic acid)$_3$Fe, or (aspartic acid)$_3$Al.

4. The spray-dried particle according to claim 2, wherein the ratio is below 5%.

5. The spray-dried particle according to claim 1, wherein said complex has the following formula (Ia):

$$(\text{Acid})_n M \qquad\qquad (\text{Ia})$$

where M represents said metal,
n being equal to 2 when said metal is divalent and to 3 when said metal is trivalent,
said complex being a salt of formula (HMTBA)$_2$Ca, (HMTBA)$_2$Mg, (HMTBA)$_2$Fe, (HMTBA)$_2$Mn, (HMTBA)$_2$Zn, (HMTBA)$_2$Cu, (HMTBA)$_3$Fe, (HMTBA)$_3$Al, (methionine)$_2$Ca, (methionine)$_2$Mg, (methionine)$_2$Fe, (methionine)$_2$Mn, (methionine)$_2$Zn, (methionine)$_2$Cu, (methionine)$_3$Fe, (methionine)$_3$Al, (aspartic acid)$_2$Ca, (aspartic acid)$_2$Mg, (aspartic acid)$_2$Fe, (aspartic acid)$_2$Mn, (aspartic acid)$_2$Zn, (aspartic acid)$_2$Cu, (aspartic acid)$_3$Fe, or (aspartic acid)$_3$Al.

6. The spray-dried particle according to claim 1, wherein said metal or corresponding cation is selected from the group consisting of Mg, Be, Ca, Sr, Ba, Mn, Fe, Co, Ni, Cu, Zn, Pt, B, Al, Ga, and In.

7. The spray-dried particle according to claim 1, wherein
said anion being 2-hydroxy-4-methyl-thiobutanoate and said cation being Ca$^{2+}$, or
said anion being methioninate or 2-hydroxy-4-methyl-thiobutanoate and said cation being selected from the group consisting of Mg$^{2+}$, Ca$^{2+}$, Fe$^{2+}$, Fe$^{2+}$, Zn$^{2+}$, Mn$^{2+}$ and Cu$^2$.

8. A pulverulent composition of more than one spray-dried particle as defined in claim 1, wherein at least one of
a granulometric size of said more than one spray-dried particle being in a range from 10 to 3000 µm in granulometric average [Dv(0.5)], or
said composition having a flowability index that is in the range from 4 to 18 [Flodex index], or
said composition being such that, for a substantial portion of said composition, a spray dried particle of said portion is agglomerated with at least one other spray-dried particle of said portion.

9. A method for preparing a pulverulent composition of more than one spray-dried particle according to claim 1, said method comprising:

a contacting step, during which said acid is brought into contact with a mineral source of said metal or corresponding cation in a spray-drying tower in order to obtain said complex or said salt, and initiate precipitation,
a spraying step, during which precipitation of said complex or said salt takes place and an ensemble of sprayed particles is formed, and
a spray-drying step, during which precipitation of said complex or said salt of said ensemble of sprayed particles proceeds until there is complete solidification of the spray-dried particles, thereby forming a stable pulverulent composition of more than one spray-dried particle.

10. The method according to claim 9,
wherein the contacting and spraying steps are carried out using a device comprising a rotating spraying element, contacting being followed immediately by spraying.

11. The method according to claim 9, further comprising:
a recovering step, during which the stable pulverulent composition of more than one spray-dried particle is collected,
wherein
the contacting step and the spraying step are performed in a spray-drying tower using a spraying device comprising a rotating spraying element, and
said spraying step immediately following said contacting step.

12. The method according to claim 9, wherein:
said contacting step is carried out by at least one of:
mixing an aqueous medium containing said acid, and an aqueous medium containing said metal or cation, and
continuous contacting of said acid with the mineral source of said metal or corresponding cation, said continuous contacting being carried out in a device selected from the group consisting of static or dynamic mixers, kneaders, extruders, mixers without an internal component and ultrasonic mixers.

13. The method according to claim 9, wherein said complex is of the following formula (Ia):

$$(\text{Acid})_n M \qquad\qquad (\text{Ia})$$

where M represents said metal,
said complex being a salt of formula (HMTBA)$_2$Ca, (HMTBA)$_2$Mg, (HMTBA)$_2$Fe, (HMTBA)$_2$Mn, (HMTBA)$_2$Zn, (HMTBA)$_2$Cu, (HMTBA)$_3$Fe, (HMTBA)$_3$Al, (methionine)$_2$Ca, (methionine)$_2$Mg, (methionine)$_2$Fe, (methionine)$_2$Mn, (methionine)$_2$Zn, (methionine)$_2$Cu, (methionine)$_3$Fe, (methionine)$_3$Al, (aspartic acid)$_2$Ca, (aspartic acid)$_2$Mg, (aspartic acid)$_2$Fe, (aspartic acid)$_2$Mn, (aspartic acid)$_2$Zn, (aspartic acid)$_2$Cu, (aspartic acid)$_3$Fe, or (aspartic acid)$_3$Al.

14. The method according to claim 9, wherein said metal or corresponding cation is selected from the group consisting of Mg, Be, Ca, Sr, Ba, Mn, Fe, Co, Ni, Cu, Zn, Pt, B, Al, Ga, and In.

15. The method according to claim 9, wherein
said anion being 2-hydroxy-4-methyl-thiobutanoate and said cation being Ca$^{2+}$, the source of Ca$^{2+}$ being selected from the group consisting of lime, milk of lime, slaked lime, calcium hydrogen carbonate, calcium carbonate and Ca(OH)$_2$, or
said anion being methioninate or 2-hydroxy-4-methyl-thiobutanoate and said cation being selected from the group consisting of Mg$^{2+}$, Ca$^{2+}$, Fe$^{2+}$, Fe$^{2+}$, Zn$^{2+}$, Mn$^{2+}$ and $Cu^{2+}$, a source of said cation being selected from oxide, hydroxide, an aqueous solution of hydroxide or a carbonate of said cation.

16. The method according to claim 9, comprising an additional step of agglomeration in a spray-drying tower which is a multiple effect spray-drying tower, and reacting said acid with said mineral metal source including agglomeration.

17. The spray-dried particle according to claim 1, wherein the amorphous fraction mass is at least 70% of the total mass of said spray-dried particle.

18. The spray-dried particle according to claim 1, wherein the amorphous fraction mass is at least 90% of the total mass of said spray-dried particle.

\* \* \* \* \*